United States Patent
Ebina

[19]

[11] Patent Number: 5,958,685
[45] Date of Patent: Sep. 28, 1999

[54] MUTANT HUMAN INSULIN RECEPTOR DNA

[75] Inventor: Yousuke Ebina, 48, Kamifukuman 3-chome, Hachiman-cho, Tokushima-shi, Tokushima 770, Japan

[73] Assignees: Otsuka Pharmaceutical Co. Ltd., Tokyo; Yousuke Ebina, Tokushima, both of Japan

[21] Appl. No.: 08/737,715

[22] PCT Filed: May 12, 1995

[86] PCT No.: PCT/JP95/00906

§ 371 Date: Feb. 7, 1997

§ 102(e) Date: Feb. 7, 1997

[87] PCT Pub. No.: WO95/31542

PCT Pub. Date: Nov. 23, 1995

[30] Foreign Application Priority Data

May 12, 1994 [JP] Japan ................................. 7-134827

[51] Int. Cl.$^6$ .............................. C12Q 1/68; C07H 21/04
[52] U.S. Cl. ............................ 435/6; 536/23.5; 536/24.31
[58] Field of Search ............................ 514/44; 536/23.1, 536/23.5, 24.3, 24.31; 435/6, 7.1

[56] References Cited

U.S. PATENT DOCUMENTS 5,260,200  11/1993  Kahn et al. ............................. 435/68.1
5,621,075  4/1997  Kahn et al. ............................. 530/350

OTHER PUBLICATIONS

Krook et al., "Rapid and simultanoues detection of multiple mutations by pooled . . ." Hum. Molec. Gene. 1(6):391–395 (1992).

Makino et al., Mini Review Insulin Receptor Gene Mutation: A Molecular Genetical and Functional Analysis Cell. Sign. 4(4):351–363 (1992).

Kan et al., "Frequency of Mutations of Insulin Receptor Gene in Japanese Patients with NIDDM" Diabetes 44:1081–1086 (1995).

*Primary Examiner*—David Guzo
*Attorney, Agent, or Firm*—Sughrue, Mion, Zinn, Macpeak & Seas, PLLC

[57] ABSTRACT

A mutant human insulin receptor DNA, wherein the base sequence encoding $Thr^{831}$ in human insulin receptor DNA has been replaced by a base sequence encoding Ala and/or the base sequence encoding $Tyr^{1334}$ therein has been replaced by a base sequence encoding Cys; a fragment of the mutant human insulin receptor DNA containing the mutation part(s); a diagnostic probe for non-insulin-dependent diabetes mellitus comprising this fragment; and a diagnostic drug for non-insulin-dependent diabetes mellitus containing this fragment.

11 Claims, 11 Drawing Sheets

Fig. 7

```
                140       150       160       170       180
              ATGGGCACCGGGGGCCGGCGGGGGGCGGCGGCCGCGCCGCTG
              MetGlyThrGlyGlyArgArgGlyAlaAlaAlaAlaProLeu
              -27
     190       200       210       220       230       240
CTGGTGGCGGTGGCCGCGCTGCTACTGGGCGCCGCGGGCCACCTGTACCCCGGAGAGGTG
LeuValAlaValAlaAlaLeuLeuLeuGlyAlaAlaGlyHisLeuTyrProGlyGluVal
                                            1
     250       260       270       280       290       300
TGTCCCGGCATGGATATCCGGAACAACCTCACTAGGTTGCATGAGCTGGAGAATTGCTCT
CysProGlyMetAspIleArgAsnAsnLeuThrArgLeuHisGluLeuGluAsnCysSer 310       320       330       340       350       360
GTCATCGAAGGACACTTGCAGATACTCTTGATGTTCAAAACGAGGCCCGAAGACTTCCGA
ValIleGluGlyHisLeuGlnIleLeuLeuMetPheLysThrArgProGluAspPheArg 370       380       390       400       410       420
GACCTCAGTTTCCCCAAACTCATCATGATCACTGATTACTTGCTGCTCTTCCGGGTCTAT
AspLeuSerPheProLysLeuIleMetIleThrAspTyrLeuLeuLeuPheArgValTyr 430       440       450       460       470       480
GGGCTCGAGAGCCTGAAGGACCTGTTCCCCAACCTCACGGTCATCCGGGGATCACGACTG
GlyLeuGluSerLeuLysAspLeuPheProAsnLeuThrValIleArgGlySerArgLeu 490       500       510       520       530       540
TTCTTTAACTACGCGCTGGTCATCTTCGAGATGGTTCACCTCAAGGAACTCGGCCTCTAC
PhePheAsnTyrAlaLeuValIlePheGluMetValHisLeuLysGluLeuGlyLeuTyr 550       560       570       580       590       600
AACCTGATGAACATCACCCGGGGTTCTGTCCGCATCGAGAAGAACAATGAGCTCTGTTAC
AsnLeuMetAsnIleThrArgGlySerValArgIleGluLysAsnAsnGluLeuCysTyr 610       620       630       640       650       660
TTGGCCACTATCGACTGGTCCCGTATCCTGGATTCCGTGGAGGATAATCACATCGTGTTG
LeuAlaThrIleAspTrpSerArgIleLeuAspSerValGluAspAsnHisIleValLeu 670       680       690       700       710       720
AACAAAGATGACAACGAGGAGTGTGGAGACATCTGTCCGGGTACCGCGAAGGGCAAGACC
AsnLysAspAspAsnGluGluCysGlyAspIleCysProGlyThrAlaLysGlyLysThr 730       740       750       760       770       780
AACTGCCCCGCCACCGTCATCAACGGGCAGTTTGTCGAACGATGTTGGACTCATAGTCAC
AsnCysProAlaThrValIleAsnGlyGlnPheValGluArgCysTrpThrHisSerHis 790       800       810       820       830       840
TGCCAGAAAGTTTGCCCGACCATCTGTAAGTCACACGGCTGCACCGCCGAAGGCCTCTGT
CysGlnLysValCysProThrIleCysLysSerHisGlyCysThrAlaGluGlyLeuCys 850       860       870       880       890       900
TGCCACAGCGAGTGCCTGGGCAACTGTTCTCAGCCCGACGACCCCACCAAGTGCGTGGCC
CysHisSerGluCysLeuGlyAsnCysSerGlnProAspAspProThrLysCysValAla 910       920       930       940       950       960
TGCCGCAACTTCTACCTGGACGGCAGGTGTGTGGAGACCTGCCCGCCCCCGTACTACCAC
CysArgAsnPheTyrLeuAspGlyArgCysValGluThrCysProProProTyrTyrHis
```

Fig. 8

```
           970       980       990       1000      1010      1020
TTCCAGGACTGGCGCTGTGTGAACTTCAGCTTCTGCCAGGACCTGCACCACAAATGCAAG
PheGlnAspTrpArgCysValAsnPheSerPheCysGlnAspLeuHisHisLysCysLys 1030      1040      1050      1060      1070      1080
AACTCGCGGAGGCAGGGCTGCCACCAATACGTCATTCACAACAACAAGTGCATCCCTGAG
AsnSerArgArgGlnGlyCysHisGlnTyrValIleHisAsnAsnLysCysIleProGlu 1090      1100      1110      1120      1130      1140
TGTCCCTCCGGGTACACGATGAATTCCAGCAACTTGCTGTGCACCCCATGCCTGGGTCCC
CysProSerGlyTyrThrMetAsnSerSerAsnLeuLeuCysThrProCysLeuGlyPro 1150      1160      1170      1180      1190      1200
TGTCCCAAGGTGTGCCACCTCCTAGAAGGCGAGAAGACCATCGACTCGGTGACGTCTGCC
CysProLysValCysHisLeuLeuGluGlyGluLysThrIleAspSerValThrSerAla 1210      1220      1230      1240      1250      1260
CAGGAGCTCCGAGGATGCACCGTCATCAACGGGAGTCTGATCATCAACATTCGAGGAGGC
GlnGluLeuArgGlyCysThrValIleAsnGlySerLeuIleIleAsnIleArgGlyGly 1270      1280      1290      1300      1310      1320
AACAATCTGGCAGCTGAGCTAGAAGCCAACCTCGGCCTCATTGAAGAAATTTCAGGGTAT
AsnAsnLeuAlaAlaGluLeuGluAlaAsnLeuGlyLeuIleGluGluIleSerGlyTyr 1330      1340      1350      1360      1370      1380
CTAAAAATCCGCCGATCCTACGCTCTGGTGTCACTTTCCTTCTTCCGGAAGTTACGTCTG
LeuLysIleArgArgSerTyrAlaLeuValSerLeuSerPhePheArgLysLeuArgLeu 1390      1400      1410      1420      1430      1440
ATTCGAGGAGAGACCTTGGAAATTGGGAACTACTCCTTCTATGCCTTGGACAACCAGAAC
IleArgGlyGluThrLeuGluIleGlyAsnTyrSerPheTyrAlaLeuAspAsnGlnAsn 1450      1460      1470      1480      1490      1500
CTAAGGCAGCTCTGGGACTGGAGCAAACACAACCTCACCACCACTCAGGGGAAACTCTTC
LeuArgGlnLeuTrpAspTrpSerLysHisAsnLeuThrThrThrGlnGlyLysLeuPhe 1510      1520      1530      1540      1550      1560
TTCCACTATAACCCCAAACTCTGCTTGTCAGAAATCCACAAGATGGAAGAAGTTTCAGGA
PheHisTyrAsnProLysLeuCysLeuSerGluIleHisLysMetGluGluValSerGly 1570      1580      1590      1600      1610      1620
ACCAAGGGGCGCCAGGAGAGAAACGACATTGCCCTGAAGACCAATGGGGACAAGGCATCC
ThrLysGlyArgGlnGluArgAsnAspIleAlaLeuLysThrAsnGlyAspLysAlaSer 1630      1640      1650      1660      1670      1680
TGTGAAAATGAGTTACTTAAATTTTCTTACATTCGGACATCTTTTGACAAGATCTTGCTG
CysGluAsnGluLeuLeuLysPheSerTyrIleArgThrSerPheAspLysIleLeuLeu 1690      1700      1710      1720      1730      1740
AGATGGGAGCCGTACTGGCCCCCCGACTTCCGAGACCTCTTGGGGTTCATGCTGTTCTAC
ArgTrpGluProTyrTrpProProAspPheArgAspLeuLeuGlyPheMetLeuPheTyr 1750      1760      1770      1780      1790      1800
AAAGAGGCCCCTTATCAGAATGTGACGGAGTTCGATGGGCAGGATGCGTGTGGTTCCAAC
LysGluAlaProTyrGlnAsnValThrGluPheAspGlyGlnAspAlaCysGlySerAsn
```

Fig. 9

```
           1810      1820      1830      1840      1850      1860
        AGTTGGACGGTGGTAGACATTGACCCACCCCTGAGGTCCAACGACCCCAAATCACAGAAC
        SerTrpThrValValAspIleAspProProLeuArgSerAsnAspProLysSerGlnAsn 1870      1880      1890      1900      1910      1920
        CACCCAGGGTGGCTGATGCGGGGTCTCAAGCCCTGGACCCAGTATGCCATCTTTGTGAAG
        HisProGlyTrpLeuMetArgGlyLeuLysProTrpThrGlnTyrAlaIlePheValLys 1930      1940      1950      1960      1970      1980
        ACCCTGGTCACCTTTTCGGATGAACGCCGGACCTATGGGGCCAAGAGTGACATCATTTAT
        ThrLeuValThrPheSerAspGluArgArgThrTyrGlyAlaLysSerAspIleIleTyr 1990      2000      2010      2020      2030      2040
        GTCCAGACAGATGCCACCAACCCCTCTGTGCCCCTGGATCCAATCTCAGTGTCTAACTCA
        ValGlnThrAspAlaThrAsnProSerValProLeuAspProIleSerValSerAsnSer 2050      2060      2070      2080      2090      2100
        TCATCCCAGATTATTCTGAAGTGGAAACCACCCTCCGACCCCAATGGCAACATCACCCAC
        SerSerGlnIleIleLeuLysTrpLysProProSerAspProAsnGlyAsnIleThrHis 2110      2120      2130      2140      2150      2160
        TACCTGGTTTTCTGGGAGAGGCAGGCGGAAGACAGTGAGCTGTTCGAGCTGGATTATTGC
        TyrLeuValPheTrpGluArgGlnAlaGluAspSerGluLeuPheGluLeuAspTyrCys 2170      2180      2190      2200      2210      2220
        CTCAAAGGGCTGAAGCTGCCCTCGAGGACCTGGTCTCCACCATTCGAGTCTGAAGATTCT
        LeuLysGlyLeuLysLeuProSerArgThrTrpSerProProPheGluSerGluAspSer 2230      2240      2250      2260      2270      2280
        CAGAAGCACAACCAGAGTGAGTATGAGGATTCGGCCGGCGAATGCTGCTCCTGTCCAAAG
        GlnLysHisAsnGlnSerGluTyrGluAspSerAlaGlyGluCysCysSerCysProLys 2290      2300      2310      2320      2330      2340
        ACAGACTCTCAGATCCTGAAGGAGCTGGAGGAGTCCTCGTTTAGGAAGACGTTTGAGGAT
        ThrAspSerGlnIleLeuLysGluLeuGluGluSerSerPheArgLysThrPheGluAsp 2350      2360      2370      2380      2390      2400
        TACCTGCACAACGTGGTTTTCGTCCCCAGAAAAACCTCTTCAGGCACTGGTGCCGAGGAC
        TyrLeuHisAsnValValPheValProArgLysThrSerSerGlyThrGlyAlaGluAsp 2410      2420      2430      2440      2450      2460
        CCTAGGCCATCTCGGAAACGCAGGTCCCTTGGCGATGTTGGGAATGTGACGGTGGCCGTG
        ProArgProSerArgLysArgArgSerLeuGlyAspValGlyAsnValThrValAlaVal 2470      2480      2490      2500      2510      2520
        CCCACGGTGGCAGCTTTCCCCAACACTTCCTCGACCAGCGTGCCCACGAGTCCGGAGGAG
        ProThrValAlaAlaPheProAsnThrSerSerThrSerValProThrSerProGluGlu 2530      2540      2550      2560      2570      2580
        CACAGGCCTTTTGAGAAGGTGGTGAACAAGGAGTCGCTGGTCATCTCCGGCTTGCGACAC
        HisArgProPheGluLysValValAsnLysGluSerLeuValIleSerGlyLeuArgHis 2590      2600      2610      2620      2630      2640
        TTCACGGGCTATCGCATCGAGCTGCAGGCTTGCAACCAGGACACCCCTGAGGAACGGTGC
        PheThrGlyTyrArgIleGluLeuGlnAlaCysAsnGlnAspThrProGluGluArgCys
```

Fig. 10

```
         2650      2660      2670      2680      2690      2700
AGTGTGGCAGCCTACGTCAGTGCGAGGACCATGCCTGAAGCCAAGGCTGATGACATTGTT
SerValAlaAlaTyrValSerAlaArgThrMetProGluAlaLysAlaAspAspIleVal 2710      2720      2730      2740      2750      2760
GGCCCTGTGACGCATGAAATCTTTGAGAACAACGTCGTCCACTTGATGTGGCAGGAGCCG
GlyProValThrHisGluIlePheGluAsnAsnValValHisLeuMetTrpGlnGluPro
          831
         2770      2780      2790      2800      2810      2820
AAGGAGCCCAATGGTCTGATCGTGCTGTATGAAGTGAGTTATCGGCGATATGGTGATGAG
LysGluProAsnGlyLeuIleValLeuTyrGluValSerTyrArgArgTyrGlyAspGlu 2830      2840      2850      2860      2870      2880
GAGCTGCATCTCTGCGTCTCCCGCAAGCACTTCGCTCTGGAACGGGGCTGCAGGCTGCGT
GluLeuHisLeuCysValSerArgLysHisPheAlaLeuGluArgGlyCysArgLeuArg 2890      2900      2910      2920      2930      2940
GGGCTGTCACCGGGGAACTACAGCGTGCGAATCCGGGCCACCTCCCTTGCGGGCAACGGC
GlyLeuSerProGlyAsnTyrSerValArgIleArgAlaThrSerLeuAlaGlyAsnGly 2950      2960      2970      2980      2990      3000
TCTTGGACGGAACCCACCTATTTCTACGTGACAGACTATTTAGACGTCCCGTCAAATATT
SerTrpThrGluProThrTyrPheTyrValThrAspTyrLeuAspValProSerAsnIle 3010      3020      3030      3040      3050      3060
GCAAAAATTATCATCGGCCCCCTCATCTTTGTCTTTCTCTTCAGTGTTGTGATTGGAAGT
AlaLysIleIleIleGlyProLeuIlePheValPheLeuPheSerValValIleGlySer 3070      3080      3090      3100      3110      3120
ATTTATCTATTCCTGAGAAAGAGGCAGCCAGATGGGCCGCTGGGACCGCTTTACGCTTCT
IleTyrLeuPheLeuArgLysArgGlnProAspGlyProLeuGlyProLeuTyrAlaSer 3130      3140      3150      3160      3170      3180
TCAAACCCTGAGTATCTCAGTGCCAGTGATGTGTTTCCATGCTCTGTGTACGTGCCGGAC
SerAsnProGluTyrLeuSerAlaSerAspValPheProCysSerValTyrValProAsp 3190      3200      3210      3220      3230      3240
GAGTGGGAGGTGTCTCGAGAGAAGATCACCCTCCTTCGAGAGCTGGGGCAGGGCTCCTTC
GluTrpGluValSerArgGluLysIleThrLeuLeuArgGluLeuGlyGlnGlySerPhe 3250      3260      3270      3280      3290      3300
GGCATGGTGTATGAGGGCAATGCCAGGGACATCATCAAGGGTGAGGCAGAGACCCGCGTG
GlyMetValTyrGluGlyAsnAlaArgAspIleIleLysGlyGluAlaGluThrArgVal 3310      3320      3330      3340      3350      3360
GCGGTGAAGACGGTCAACGAGTCAGCCAGTCTCCGAGAGCGGATTGAGTTCCTCAATGAG
AlaValLysThrValAsnGluSerAlaSerLeuArgGluArgIleGluPheLeuAsnGlu 3370      3380      3390      3400      3410      3420
GCCTCGGTCATGAAGGGCTTCACCTGCCATCACGTGGTGCGCCTCCTGGGAGTGGTGTCC
AlaSerValMetLysGlyPheThrCysHisHisValValArgLeuLeuGlyValValSer 3430      3440      3450      3460      3470      3480
AAGGGCCAGCCCACGCTGGTGGTGATGGAGCTGATGGCTCACGGAGACCTGAAGAGCTAC
LysGlyGlnProThrLeuValValMetGluLeuMetAlaHisGlyAspLeuLysSerTyr
```

Fig. 11

```
           3490      3500      3510      3520      3530      3540
       CTCCGTTCTCTGCGGCCAGAGGCTGAGAATAATCCTGGCCGCCCTCCCCCTACCCTTCAA
       LeuArgSerLeuArgProGluAlaGluAsnAsnProGlyArgProProProThrLeuGln 3550      3560      3570      3580      3590      3600
       GAGATGATTCAGATGGCGGCAGAGATTGCTGACGGGATGGCCTACCTGAACGCCAAGAAG
       GluMetIleGlnMetAlaAlaGluIleAlaAspGlyMetAlaTyrLeuAsnAlaLysLys 3610      3620      3630      3640      3650      3660
       TTTGTGCATCGGGACCTGGCAGCGAGAAACTGCATGGTCGCCCATGATTTTACTGTCAAA
       PheValHisArgAspLeuAlaAlaArgAsnCysMetValAlaHisAspPheThrValLys 3670      3680      3690      3700      3710      3720
       ATTGGAGACTTTGGAATGACCAGAGACATCTATGAAACGGATTACTACCGGAAAGGGGGC
       IleGlyAspPheGlyMetThrArgAspIleTyrGluThrAspTyrTyrArgLysGlyGly 3730      3740      3750      3760      3770      3780
       AAGGGTCTGCTCCCTGTACGGTGGATGGCACCGGAGTCCCTGAAGGATGGGGTCTTCACC
       LysGlyLeuLeuProValArgTrpMetAlaProGluSerLeuLysAspGlyValPheThr 3790      3800      3810      3820      3830      3840
       ACTTCTTCTGACATGTGGTCCTTTGGCGTGGTCCTTTGGGAAATCACCAGCTTGGCAGAA
       ThrSerSerAspMetTrpSerPheGlyValValLeuTrpGluIleThrSerLeuAlaGlu 3850      3860      3870      3880      3890      3900
       CAGCCTTACCAAGGCCTGTCTAATGAACAGGTGTTGAAATTTGTCATGGATGGAGGGTAT
       GlnProTyrGlnGlyLeuSerAsnGluGlnValLeuLysPheValMetAspGlyGlyTyr 3910      3920      3930      3940      3950      3960
       CTGGATCAACCCGACAACTGTCCAGAGAGAGTCACTGACCTCATGCGCATGTGCTGGCAA
       LeuAspGlnProAspAsnCysProGluArgValThrAspLeuMetArgMetCysTrpGln 3970      3980      3990      4000      4010      4020
       TTCAACCCCAAGATGAGGCCAACCTTCCTGGAGATTGTCAACCTGCTCAAGGACGACCTG
       PheAsnProLysMetArgProThrPheLeuGluIleValAsnLeuLeuLysAspAspLeu 4030      4040      4050      4060      4070      4080
       CACCCCAGCTTTCCAGAGGTGTCGTTCTTCCACAGCGAGGAGAACAAGGCTCCCGAGAGT
       HisProSerPheProGluValSerPhePheHisSerGluGluAsnLysAlaProGluSer 4090      4100      4110      4120      4130      4140
       GAGGAGCTGGAGATGGAGTTTGAGGACATGGAGAATGTGCCCCTGGACCGTTCCTCGCAC
       GluGluLeuGluMetGluPheGluAspMetGluAsnValProLeuAspArgSerSerHis 4150      4160      4170      4180      4190      4200
       TGTCAGAGGGAGGAGGCGGGGGGCCGGGATGGAGGGTCCTCGCTGGGTTTCAAGCGGAGC
       CysGlnArgGluGluAlaGlyGlyArgAspGlyGlySerSerLeuGlyPheLysArgSer 4210      4220      4230      4240      4250      4260
       TACGAGGAACACATCCCTTACACACACATGAACGGAGGCAAGAAAAACGGGCGGATTCTG
       TyrGluGluHisIleProTyrThrHisMetAsnGlyGlyLysLysAsnGlyArgIleLeu
                            1334
           4270      4280
       ACCTTGCCTCGGTCCAATCCTTCCTAA
       ThrLeuProArgSerAsnProSer***
```

MUTANT HUMAN INSULIN RECEPTOR DNA

This application is a 371 of PCT/JP95/00906, filed May 12, 1995.

1. Technical Field

This invention relates to abnormalities in the insulin receptor structure gene in non-insulin-dependent diabetes mellitus (hereinafter referred to simply as NIDDM). More particularly, it relates to mutant human insulin receptor DNAs having mutations at specific sites and fragments thereof.

2. Background Art

NIDDM, which is a genetic disease with one of the highest incidence in mankind today, is induced by several gene abnormalities combined with environmental factors such as obesity, stress and aging. In Japan, the number of patients with NIDDM is estimated to be about 5,000,000. NIDDM has been recently designated as one of the four most serious diseases following cancer, cerebral stroke and heart infarction. Thus there has been an urgent need to establish an effective countermeasure for NIDDM. In general, the symptoms of NIDDM can be frequently ameliorated by diet therapy and kinesitherapy. Therefore, if possible, it is best to diagnose NIDDM at an early stage. Presently, in order to diagnose NIDDM at an early stage, troublesome examinations, such as OGTT, must be conducted. OGTT comprises orally administering 75 g of glucose to a patient in a fasting state, collecting the blood at intervals of 30 minutes and measuring the blood sugar level at two hour intervals. Therefore, a more convenient and reliable diagnostic method is needed for early detection and prevention of NIDDM.

Although no gene has been found to be responsible for the onset of NIDDM, it is assumed that genes of insulin function mechanism-relating factors or genes of insulin secretion-relating factors may be candidate genes for NIDDM. It is known that the factors relating to insulin function involve insulin receptor, insulin receptor substrate (IRS-1), glucose transporter type 4, etc., while the factors relating to insulin secretion involve glucose transporter type 2, glucokinase, chondriogene, etc. Although attempts were made to detect abnormalities in the latter two genes in association with NIDDM, the abnormality ratio was only around 1% in each case (Interim Report in 1993, Onset Mechanism Group, Research and Study Project on Diabetes, Ministry of Health and Welfare).

Insulin acts upon the target cell by binding to the insulin receptor located on the cell membranae. Insulin resistance is often observed in the early stages of NIDDM (Taylor, S. I. Diabetes 41:1473–1490, 1992). Based on these facts, it has been speculated that the insulin receptor might be the gene responsible for the onset of NIDDM. Abnormalities in the insulin receptor would result in a high insulin resistance and thus induce severe diabetes accompanied by hyperinsulinemia. However, such a phenomenon is scarcely observed in NIDDM cases. Thus, abnormalities in the insulin receptor have not been related to NIDDM.

In recent years, a number of insulin receptor abnormalities have been discovered by others including the present inventors. It has been found that the examination data and symptoms of patients vary widely depending on the mutation type (M. Taira et al., Science 245:63–66, 1989; F. Shimada et al., Lancet 335:1179–1181, 1990). Thus, it is quite possible that insulin receptor gene abnormalities may partially participate in the onset of NIDDM. However, no attempt has been made so far to systematically detect the insulin receptor gene abnormalities on a large scale in association with NIDDM. In addition, the particular locations of the gene abnormalities are still unknown.

Under these circumstances, the present inventors have prepared chromosomal DNAs from the blood of typical NIDDM Japanese patients and studied the base sequences of insulin receptor DNAs in order to reveal the relationship between human insulin receptor gene abnormalities and NIDDM. As a result, they have found out that a quantitative abnormality is observed at a significant frequency in the patients with NIDDM, thus completing the present invention.

BRIEF DESCRIPTION OF THE DRAWINGS

FIG. 7 shows DNA (SEQ ID NO:1) (No. 1) encoding human insulin receptor.

FIG. 8 shows DNA (No. 2) encoding human insulin receptor.

FIG. 9 shows DNA (No. 3) encoding human insulin receptor.

FIG. 10 shows DNA (No. 4) encoding human insulin receptor, wherein the mutation part (the amino acid at the 831-position) is boxed.

FIG. 11 shows DNA (No. 5) encoding human insulin receptor, wherein the mutation part (the amino acid at the 1334-position) is boxed.

DETAILED DESCRIPTION OF THE INVENTION

Figure 1:
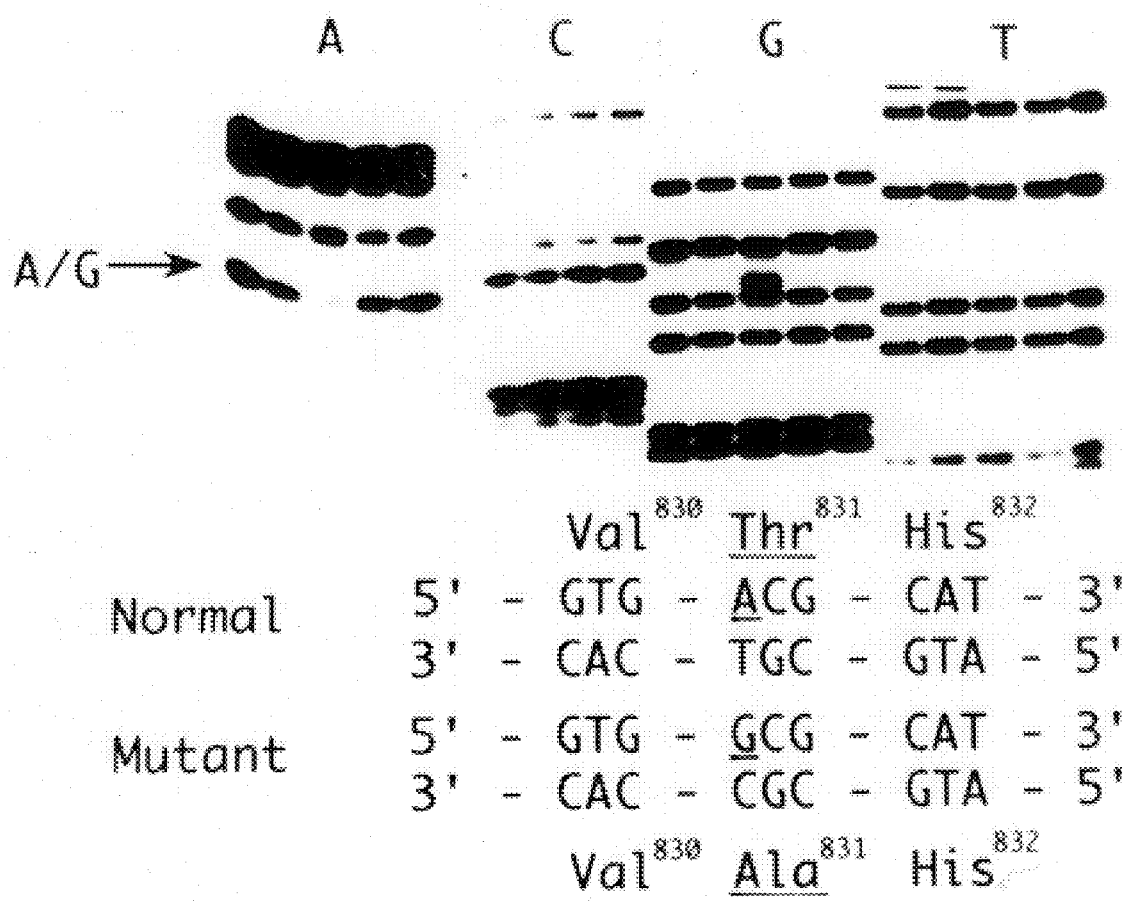
FIG. 1 is an electrophorogram which shows part of the base sequence of the exon 13 of the insulin receptor β-subunit of five patients with NIDDM.

The present invention provides a mutant human insulin receptor DNA, wherein the base sequence encoding Thr$^{831}$ in human insulin receptor DNA has been replaced by a base sequence encoding Ala and/or the base sequence encoding Tyr$^{1334}$ therein has been replaced by a base sequence encoding Cys, or a fragment of this mutant human insulin receptor DNA containing the mutation part(s).

The insulin receptor is a biomembrane receptor which specifically binds to insulin and thus transmits the information to the inside of cells. It consists of two α chains (735 residues, molecular weight: 84, 214) and two β chains (620 residues, molecular weight: 69, 700). The insulin receptor gene consists of 22 exons among which 11 exons encode the α subunits while other 11 exons encode the β-subunits (S. Seino et al., Proc. Natl. Acad. Sci. USA 86:114–118, 1989). The base sequence of human insulin receptor and the amino acid sequence corresponding thereto are shown in SEQ ID NO:1 in Sequence Listing. The mutant human insulin receptor DNA of the present invention is one wherein the base sequence (<u>A</u>CG) encoding Thr$^{831}$ in the exon 13 of the β-subunit of human insulin receptor DNA has been replaced by a base sequence (<u>G</u>CG) encoding Ala and/or the base sequence (T<u>A</u>C) encoding Tyr$^{1334}$ in the exon 22 of the β-subunit has been replaced by a base sequence (T<u>G</u>C) encoding Cys, and a fragment of said mutant human insulin receptor DNA containing the mutation. The mutation parts of the mutant human insulin receptor of the present invention are boxed in the sequences shown in FIGS. 7 to 11 identical with the sequence represented by SEQ ID NO:1 in Sequence Listing.

The mutant human insulin receptor DNA of the present invention is obtained by amplifying all of the 22 exon genes of the insulin receptor of 51 typical Japanese patients with NIDDM by PCR (polymerase chain reaction) and inserting the PCR products thus amplified into the pUC19 vector followed by DNA sequencing. As the result of the DNA sequencing, three patients had a heterozygous missense mutation Thr$^{831}$→Ala$^{831}$ in the exon 13 of the β-subunit and one patient had a heterozygous missense mutation Tyr$^{1334}$→Cys$^{1334}$ in the exon 22 of the β-subunit.

The amino acid replacement observed in the former mutation (Thr$^{831}$→Ala$^{831}$) has never been reported hitherto. Although this mutation was induced on cDNA and forced to express in animal cells in order to analyze the receptor function, no remarkable disorder in the receptor function was observed. Furthermore, this mutation was not observed in 272 healthy volunteers. Thus statistical analyses indicate that this mutation relates to the onset of NIDDM. To further examine the relationship between this mutation (IR$^{831}$) and the onset of NIDDM, the data on a family having the mutant IR$^{A831}$ were analyzed. As a result, it is strongly suggested that the heterozygous mutation of IR$^{A831}$ would cause the onset of NIDDM.

Similarly, no remarkable disorder in the receptor function is observed in association with the latter mutation (Tyr$^{1334}$→Cys$^{1334}$). As the result of analyses of a family, it was considered that this mutation does not relate to the onset of NIDDM. However, the insulin receptor having this mutation cannot bind to PI 3-kinase and the present inventors have recently proven that PI 3-kinase participates in the insulin signal transmission, particularly, translocation of glucose transporter (F. Kanai et al., Biochem. Biophys. Res. Commun. 195:762–768, 1993). Accordingly, it is suggested that this mutation might relate to the onset of NIDDM.

The mutant human insulin receptor DNA of the present invention amounts to at least 6% of the quantitative mutations of the genes responsible for the onset of NIDDM, which is a level significant enough to ensure the application thereof to gene diagnosis of NIDDM. There are a number of genes participating in the onset of NIDDM and mutations in each of these gene have hot spots. It is assumed that several hot spots, including the mutation parts of the above-mention as well as the present invention, would be considered major ones. Supposing that other mutations participating in the onset of NIDDM could be clarified, the combined use thereof with the mutant human insulin receptor DNA of the present invention or its fragment can provide a convenient and reliable method of gene diagnosis for NIDDM. It is expected, furthermore, that the early diagnosis of NIDDM with the combined use of this gene diagnosis and the conventional diagnostic methods largely contributes to the appropriate prevention and treatment of NIDDM.

The mutant human insulin receptor DNA of the present invention, its fragment, DNAs complementary thereto and their fragments, are useful as a diagnostic probe to be used in the above-mentioned diagnosis. The following DNA fragments are usable as the diagnostic probe for NIDDM according to the present invention:

(a) a mutant human insulin receptor DNA fragment wherein the base sequence (ACG) encoding Thr$^{831}$ in the exon 13 of the β-subunit of human insulin receptor DNA has been replaced by a base sequence (GCG) encoding Ala;

(b) a mutant human insulin receptor DNA fragment wherein the base sequence (TAC) encoding Tyr$^{1334}$ in the exon 22 of the β-subunit of human insulin receptor DNA has been replaced by a base sequence (TGC) encoding Cys; and (c) a DNA fragment which is complementary to the mutant human insulin receptor DNA fragment of the above (a) or (b).

Such a DNA fragment for a diagnostic probe is generally composed of up to about 100 bases containing the above-mentioned mutation part, preferably from 10 to 50 bases containing the above-mentioned mutation part and still preferably from 10 to 30 bases containing the above-mentioned mutation part.

The DNA or DNA fragment of the present invention can be synthesized in accordance with the base sequence of the present invention by using an automatic DNA synthesizer with the use of, for example, the solid phase method performed on a support such as silica.

The above-mentioned gene diagnosis according to the present invention is not particularly restricted in procedures, etc. and various methods may be selected therefor over a wide range, so long as it aims at detecting the above-mentioned specific mutation(s) characterized by the present invention. Since the gene mutations to be detected by the present invention have been clarified and specified, those skilled in the art can easily select appropriate methods therefor in accordance with the disclosure of the present invention.

For example, this method can be established by analyzing the base sequence of a specific site as defined above, which falls within the scope of the present invention as a matter of course. It therefor seems reasonable to employ Southern hybridization or dot hybridization (each described in Southern, E. M., J. Mol. Biol., 98:503–517, 1975). It is preferable to use a combination of PCR with a gene amplification procedure, since highly sensitive and accurate detection can be conveniently and easily performed with the use of a small amount of DNA specimen. Examples of such a combination include PCR-RFLP (restriction fragment length polymorphism) analysis, PCR-single strand polymorphism analysis (Orita, M., Iwahata, H. Kanazawa, H., Hayashi, K. and Sekiya, T., Proc. Natl. Acad. Sci., USA, 86:2766–2770, 1989), PCR-SSO (specific sequence oligonucleotide) method, PCR-ASO (allele specific oligomer) nucleotide method with the use of dot hybridization (Saiki, R. K., Bugawan, T. L., Horn, G. T., Mullis, K. B. and Erich, H. A, Nature, 324:163–166, 1986), etc.

In the present invention, it is particularly preferable to use the RFLP analysis and/or allele specific hybridization method from the viewpoint of convenience. This detection method will be described in greater detail.

Various operations employed in the detection method of the present invention (for example, chemical synthesis of partial DNA, enzymatic treatments for the cleavage, deletion, addition or binding of DNA, isolation, purification, replication and selection of DNA, etc.) can be each carried out in the conventional manner [Bunshi Idengaku Jikken-ho (Experimental Methods for Molecular Genetics), Kyoritsu Shuppan, 1983; PCR Technology, Takara Shuzo, 1990]. For example, DNA can be isolated and purified by agarose gel electrophoresis, etc. DNA can be sequenced by the dideoxy sequencing method (Sanger, F., Nicklen, S. and Coulson, A. R., Proc. Natl. Acad. Sci., USA, 74:5463–5467, 1977), Maxam-Gilbert method (Maxam, A. M. and Gilbert, W., Method in Enzymology, 65:499–560, 1980), etc. Alternatively, DNA sequencing can be easily carried out by using marketed sequence kits, etc. Also, PCR for amplifying a specific region of DNA can be carried out in accordance with the conventional method (see, for example, Saiki, R. K., Scharf, S., Faloona, F. A., Mullis, K. B., Horn, G. T., Erlich, H. A. and Arnheim, N., Science, 230:1350–1354, 1985). These fundamental operations are employed in, for example, the references cited herein which are provided by way of reference similar to the Examples presented hereinbelow.

The genomic DNA to be assayed by the detection method of the present invention may be obtained from any source, so long as it is a sample originating in a human being and containing the genomic DNA. The genomic DNA can be extracted and purified from such a sample in accordance with the conventional method.

From this genomic DNA, a DNA region containing the mutation site relating to the present invention is amplified. Thus a concentrated specimen can be obtained in a large amount. For example, PCR can be performed with the use of appropriate primers by which a region containing the above-mentioned mutation in the exon 13 or 22 alone can be specifically amplified. These primers can be selected in the conventional manner. The base length of the region to be amplified is not particularly restricted but usually regulated to 100 to 500 bp. It is proper to employ, for example, primers homologous to the flanking intronic sequence (Seino, S., Seino, M. and Bell, Gl., Diabetes, 39:123–128, 1990) which were employed in Examples given hereinafter in order to amplify a region including the exon 13. To amplify a region including the exon 22, use can be made of, for example, a sense primer (5'-CACTGACCTCATGCGCATGTGCTGG-3') (SEQ ID NO:3) and an antisense primer (5'-ATTGGACCGAGGCAAGGTCAGAAT-3') (SEQ ID NO:4) are employed. By using these primers, the desired regions as described above can be obtained as amplified DNA fragments of 322 bp (exon 13) and 346 bp (exon 22) respectively.

By using the desired DNA region which has been amplified by PCR, the specific mutation of the present invention contained in this region can be detected and confirmed. In the Examples given hereinafter, the mutation in the exon 13 was detected by the RFLP method. The mutation at Ala$^{831}$ (G̲CG) results in the specific cleavage site of the restriction enzyme CfoI. When the above-mentioned PCR amplification product of the exon 13 (322 bp) having this mutation is digested with CfoI, therefore, two fragments (102 bp, 220 bp) are obtained. In contrast, no such cleavage occurs in the mutation-free wild type (322 bp). The fragments thus formed are identified as specific bands by the conventional method.

To detect the mutation in the exon 22, use is made of allele-specific hybridization wherein the above-mentioned DNA fragment for diagnostic probe is employed. This hybridization can be performed in a conventional manner, so long as it aims at detecting the mutation as specified in the present invention with the use of the specific diagnostic probe as described above. For example, the following conditions were employed in Examples given hereinafter.

The PCR amplification product (346 bp) of the exon 22 as described above, which had been transferred onto a nitrocellulose filter, was hybridized overnight at 30° C. in a probe solution containing 6× SSC, 10× Denhardt's solution, 1% of SDS, 1 mg/ml of salmon sperm DNA and a $^{32}$P-labeled probe. The hybridized filter was washed twice with 6× SSC in 0.1% of SDS at 54° C. each for 20 minutes and then autoradio-graphed. The probe specific to the IR$^{C1334}$ mutation (Cys$^{1334}$:TG̲C), by which it is distinguishable from the wild type (Tyr$^{1334}$:TA̲C), employed herein was the $^{32}$P-labeled probe 5'-ATGTGTGTGC̲AAGGGATGT-3' (SEQ ID NO:5).

The occurrence of the mutation of the present invention can be detected by observing the pattern of the bands thus obtained (two hybridized bands of 102 bp and 220 bp assignable to the mutation in the exon 13, or one of 346 bp assignable to the mutation in the exon 22) and confirming the same.

In this gene diagnosis, it is advantageous to utilize a diagnostic drug which contains as the active ingredient a means or reagent for detecting the occurrence of the mutation according to the present invention. Therefore, the present invention further provides such a drug for the diagnosis of non-insulin-dependent diabetes mellitus. This diagnostic drug contains as the essential ingredient a specific reagent suitable for the method for detecting the occurrence of the mutation of the present invention. This specific reagent may be appropriately selected depending on the employed detection method. It is characterized by being necessary in the means for specifically detecting the mutation of the present invention, for example, the DNA fragment for diagnostic probe as described above and/or a specific restriction enzyme. Although a reagent for PCR-amplifying specifically a region of the mutation of the present invention (for example, a primer designed therefor, etc.) cannot be regarded as the essential ingredient of the diagnostic drug of the present invention, the diagnostic drug of the present invention may contain such a reagent together with the reagent(s) for hybridization.

To further illustrate the present invention in greater detail, and not by way of limitation, the following Examples will be given.

EXAMPLES

Example 1
Separation of human chromosomal DNA

Ten ml portions of blood of about 100 typical Japanese patients with NIDDM were provided by Dr. Makino et al. of the Second Department of Internal Medicine, Faculty of Medicine, Chiba University. Human chromosomal DNA was separated in the following manner.

1) Into two 50 ml blue-capped tubes were introduced 45 ml portions of solution A [0.32 M of sucrose, 10 mM of Tris-HCl (pH 7.5), 5 mM of $MgCl_2$ and 1% of Triton X-100] with a 10 ml graduated pipet.

2) The blood was collected in an amount of about 10 ml.

3) About 5 ml portions of the blood were added to the two blue-capped tubes containing the solution A followed by end-over-end mixing.

4) Each mixture was centrifuged at 4° C. for 10 minutes at 3,000 rpm.

5) The supernatant was carefully discarded and the tube was placed upside-down on Kim-Wipe to thereby eliminate the solution.

6) Into this tube was introduced 4 ml of solution B [0.075 M of NaCl, 0.024 M of EDTA (pH 8.0)] with a 5 ml graduated pipet. After mixing, pellets were peeled off from the bottom of the tube, transferred into another tube and mixed well with a vortex mixer.

7) To this mixture was added 1 ml of solution C (containing equivalent amounts of 5% of SDS and 2 mg/ml of proteinase K) with an automatic pipet. After mixing well, the mixture was reacted overnight at 37° C.

8) Five ml of a phenol solution was added thereto with a 5 ml graduated pipet and, after capping, mixed well. Further, 5 ml of a mixture of chloroform with isoamyl alcohol (24:1) was added thereto and, after capping, mixed well.

9) The whole solution was transferred into an orange-capped conical tube (15 ml) and centrifuged at 3,000 rpm for 10 minutes.

10) The supernatant was taken up carefully with a Pasteur pipet having a cut-off tip and transferred into a fresh orange-capped tube. Then 5 ml of a mixture of phenol with chloroform (1:1) was added thereto and mixed for 30 minutes.

11) The mixture was centrifuged at 3,000 rpm for 10 minutes.

12) The supernatant was taken up carefully with a Pasteur pipet having a cut-off tip and transferred into a blue-capped tube (50 ml).

13) After adding 0.5 ml of solution D (3 M sodium acetate) with an automatic pipet, capping and mixing, 10 ml of cold ethanol (99.9%) was slowly layered thereon with a graduated pipet.

14) After capping, the mixture was slowly mixed end-over-end. Thus, the chromosomal DNA was obtained as a white insoluble matter. It was scooped up with a Pasteur pipet having a bowed tip and gently immersed in 1 ml of a 70% ethanol solution for about 15 seconds. Next, the insoluble matter was transferred into an Eppendorf tube containing 200 μl of solution E [10 mM of Tris-HCl (pH 7.5), 1 mM of EDTA).

15) The Eppendorf tube was capped and the contents were mixed with a vortex mixer several times to thereby well dissolve the DNA.

Similarly, chromosomal DNA was separated from 272 healthy volunteers.

Example 2
Amplification of insulin receptor gene exons by PCR, subcloning thereof and isolation of plasmid DNA In accordance with the method of Seino et al. (Proc. Natl. Acad. Sci. USA 86:114–118, 1989; Diabetes 39:123–128, 1990), the insulin receptor gene was amplified by PCR with the use of primer DNAs by which all of 22 exons of the insulin receptor gene could be amplified.

Namely, 99 μl of mixed solution F of the following composition was introduced into a 0.5 ml tube. Next, 1 μl (1 μg) of the DNA was added thereto and mixed therewith.

| | (Volume) | (Final) |
|---|---|---|
| 10 x reaction buffer | 10.0 μl | 1 x |
| dNTPs mix (2.5 mM) | 8.0 μl | 200 μM |
| upstream primer | 0.5 μl | 50 pmol/100 μl |
| downstream primer | 0.5 μl | 50 pmol/100 μl |
| $H_2O$ | 79.5 μl | |
| Ampli Taq ™ polymerase | 0.5 μl | 2.5 U/assay |
| total | 99.0 μl. | |

Mineral oil was layered onto the above mixture so as to prevent the sample from evaporating. To improve the heat conductivity, a drop of mineral oil was further added to each well of the heat box. By using them, PCR was performed under the conditions as specified below.

| | |
|---|---|
| 1. Initial denaturation | 94° C., 3 minutes. |
| 2. Denaturation | 94° C., 1 minute. |
| 3. Annealing | 53° C., 1.5 minutes × 30 cycles. |
| 4. Extension | 72° C., 2.5 minutes, terminated at 72° C., 4 minutes. |

To the sample thus amplified by PCR was added 100 μl of chloroform. After mixing well with a vortex mixer, the mixture was centrifuged for 1 minute. Then the lower layer was thoroughly eliminated with a Pasteur pipet and DNA was obtained from the upper layer.

The PCR amplified DNA fragments thus obtained were purified by agarose gel electrophoresis and ligated to the HincII site of pUC19 which had been treated with alkaline phosphatase. Then these recombinants were introduced into *Escherichia coli*. From several hundred colonies tolerant to ampicillin, 12 colonies were picked up. Then it was thus confirmed for each exon that more than 50% of the colonies had a PCR DNA fragment. All of the remaining colonies were scratched off from the agar medium and grown in a liquid medium. Then crude plasmid DNAs were separated by the alkaline lysis method and RNAs were removed by precipitation with polyethylene glycol. It is considered that, when a number of E. coli transformants are used as in the case of the present Example, the patroclinal PCR products and the matroclinal ones are obtained almost in the same amount. Accordingly, the base sequences of the DNAs thus separated have both of the patroclinal and matroclinal gene sequences therein.

Example 3

DNA sequencing

The DNA fragments obtained in Example 2 were sequenced by the dideoxy sequencing method with the use of in isotope (Maxam, A. M. and Gilbert, W., Proc. Natl. Acad. Sci. USA 74:560–564, 1977). In brief, the primers employed in the DNA amplification by PCR were hybridized with the DNA fragments. Then DNAs were synthesized with Sequenase by using isotope-labeled dCTP, followed by electrophoresis and autoradiography.

As a result, mutations free from any amino acid replacement were found in ten patients while mutations accompanied by amino acid replacement were found in four patients.

Among the four patients with mutations accompanied by amino acid replacement as described above, three patients showed the mutation (Thr$^{831}$→Ala$^{831}$) in the exon 13 of the insulin receptor β-subunit, as shown below.

|         | Val$^{830}$ - Thr$^{831}$ - His$^{832}$ |       |       |      |
|---------|-------|-------|-------|------|
| normal  | 5' - GTG | - ACG | - CAT | - 3' |
|         | 3' - CAC | - TGC | - GTA | - 5' |
| mutant  | 5' - GTG | - GCG | - CAT | - 3' |
|         | 3' - CAC | - CGC | - GTA | - 5' |
|         | Val$^{830}$ - Ala$^{831}$ - His$^{832}$ |       |       |      |

FIG. 1 is an electrophorogram which shows a part of the DNA base sequence of the exon 13 of the insulin receptor β-subunit of five patients with NIDDM involving those having the above mutation. It was found that the patient of the third lane was a heterozygote having both of the sequences Thr$^{831}$ (ACG) and Ala$^{831}$ (GCG). Two other patients had the same sequences.

On the other hand, the remaining patient having mutation accompanied with amino acid replacement showed the following mutation (Tyr$^{1334}$→Cys$^{1334}$) in the exon 22 of the insulin receptor β-subunit, as shown below.

|         | Pro$^{1333}$ - Tyr$^{1334}$ - Thr$^{1335}$ |       |       |      |
|---------|-------|-------|-------|------|
| normal  | 5' - CCT | - TAC | - ACA | - 3' |
|         | 3' - GGA | - ATG | - TGT | - 5' |
| mutant  | 5' - CCT | - TGC | - ACA | - 3' |
|         | 3' - GGA | - ACG | - TGT | - 5' |
|         | Pro$^{1333}$ - Cys$^{1334}$ - Thr$^{1335}$ |       |       |      |

Figure 2:
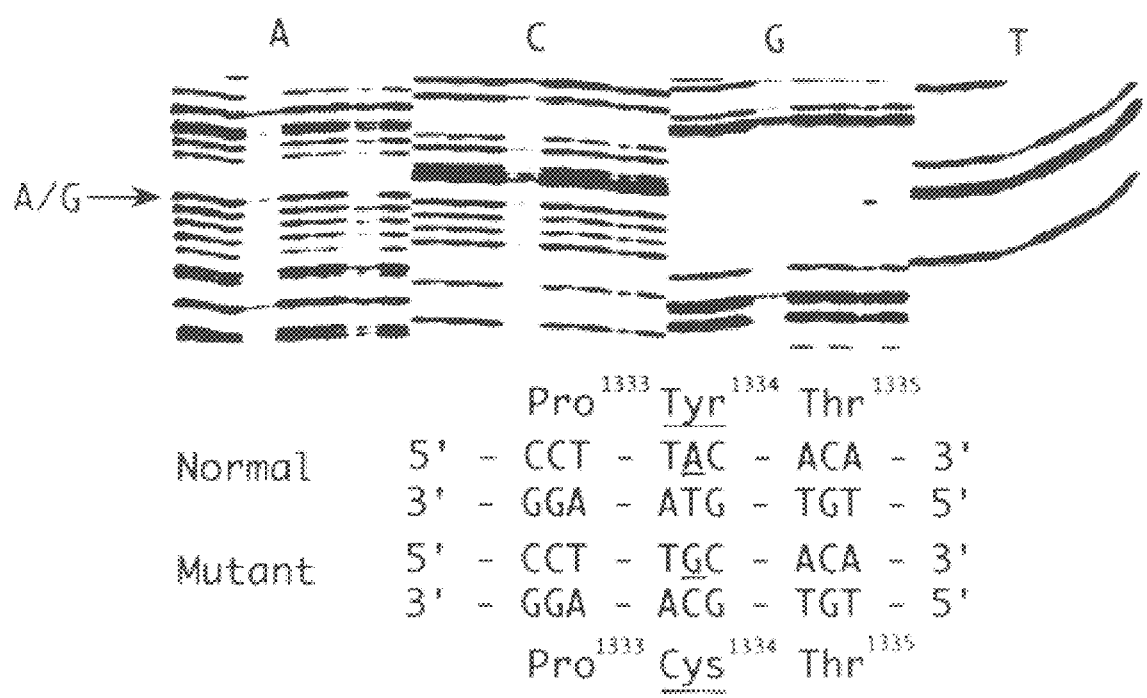
FIG. 2 is an electrophorogram which shows part of the base sequence of the exon 22 of the insulin receptor β-subunit of eight patients with NIDDM.

FIG. 2 is an electrophorogram which shows a part of the DNA base sequence of the exon 22 of the insulin receptor β-subunit of eight patients with NIDDM involving the one having the above mutation. It was found that the patient of the seventh lane was a heterozygote having both of the sequences Tyr$^{1334}$ (TAC) and Cys$^{1334}$ (TGC).

Example 4

Functional characterization of mutant insulin receptors expressed in mammalian cells Test Method (1) Construction of expression plasmids By using PCR on cDNA, two artificially mutated cDNAs, i.e., insulin receptors IR$^{A831}$ having the mutation (Thr$^{831}$→Ala$^{831}$) and IR$^{C1334}$ having the mutation (Tyr$^{1334}$→Cys$^{1334}$) were constructed.

Next, the artificial mutant cDNAs IR$^{A831}$ and IR$^{C1334}$ were subcloned into a mammalian expression vector SRα (Y. Tanabe et al., Mol. Cell Biol. 8:446–472, 1988) to thereby give SRαIR$^{A831}$ and SRαIR$^{C1334}$ respectively. The wild type insulin receptor SRαIR$^{WT}$ employed as the control was constructed by a method of F. Kanai et al. (J. Bio. Chem. 268:14523–14526, 1993).

(2) Establishment of CHO cells expressing the wild type and artificial mutant insulin receptors CHO cells were transfected with SRαIR$^{WT}$, SRαIR$^{A831}$ or SRαIR$^{C1334}$ (each 10 μg) and pSV2-neo (1 μg). After selecting with 400 μg/ml of G418 (Sigma), cells expressing human insulin receptors were identified by $^{125}$I-labeled insulin binding in accordance with the method of H. Hayashi et al. (Biochem. J. 280:769–775, 1991). The number of cell surface receptors was calculated by Scatchard analysis (G. Scathard, Ann. NY Acad. Sci. 51:660–672, 1949).

(3) Assay of receptor tyrosine kinase activities

By using the method of Hayashi et al. (Biochem. J. 280:769–775, 1991), the insulin-stimulated receptor autophosphorylation of IR$^{WT}$ and IR$^{A831}$ was performed in a 96-well plate. The incorporation of $^{32}$P into the receptor β-subunit was detected by 6% SDS-PAGE and measured by a Bio-image-analyzer BAS2000.

(4) Insulin-induced complex formation of insulin receptors and α-type p85 subunit of PI 3-kinase.

To transiently express both of the α-type p85 subunit of PI 3-kinase and wild type or mutant IRs, COS-7 cells were transfected with SRαp85α (1.5 μg) and SRαIR, SRαIR$^{A831}$ or SRαIR$^{C1334}$ (each 1.5 μg), respectively by using Lipofectamine™ Reagent (Bethesda Research Laboratories). After stimulating with 10$^{-7}$ M of insulin for 10 minutes, cell lysates were prepared and incubated with an anti-IR antibody 1G2, which recognizes the β-subunit of IR, or a rabbit polyclonal anti-p85α antibody, and protein G-Sepharose. The immunoprecipitates were electrophoresed on a 6% SDS-PAGE. Immunoblotting was performed by using an anti-phosphotyrosine antibody (PY20) or an anti-insulin receptor antibody 3B11 which recognizes the α-subunit of IR.

Results (1) A831 mutation

Examination was made on two clones stably expressing IR$^{WT}$ (clone Nos. 12 and 21) and two clones stably expressing IR$^{A831}$ (clone Nos. 10 and 17) obtained in the above test method (2).

Figure 3:
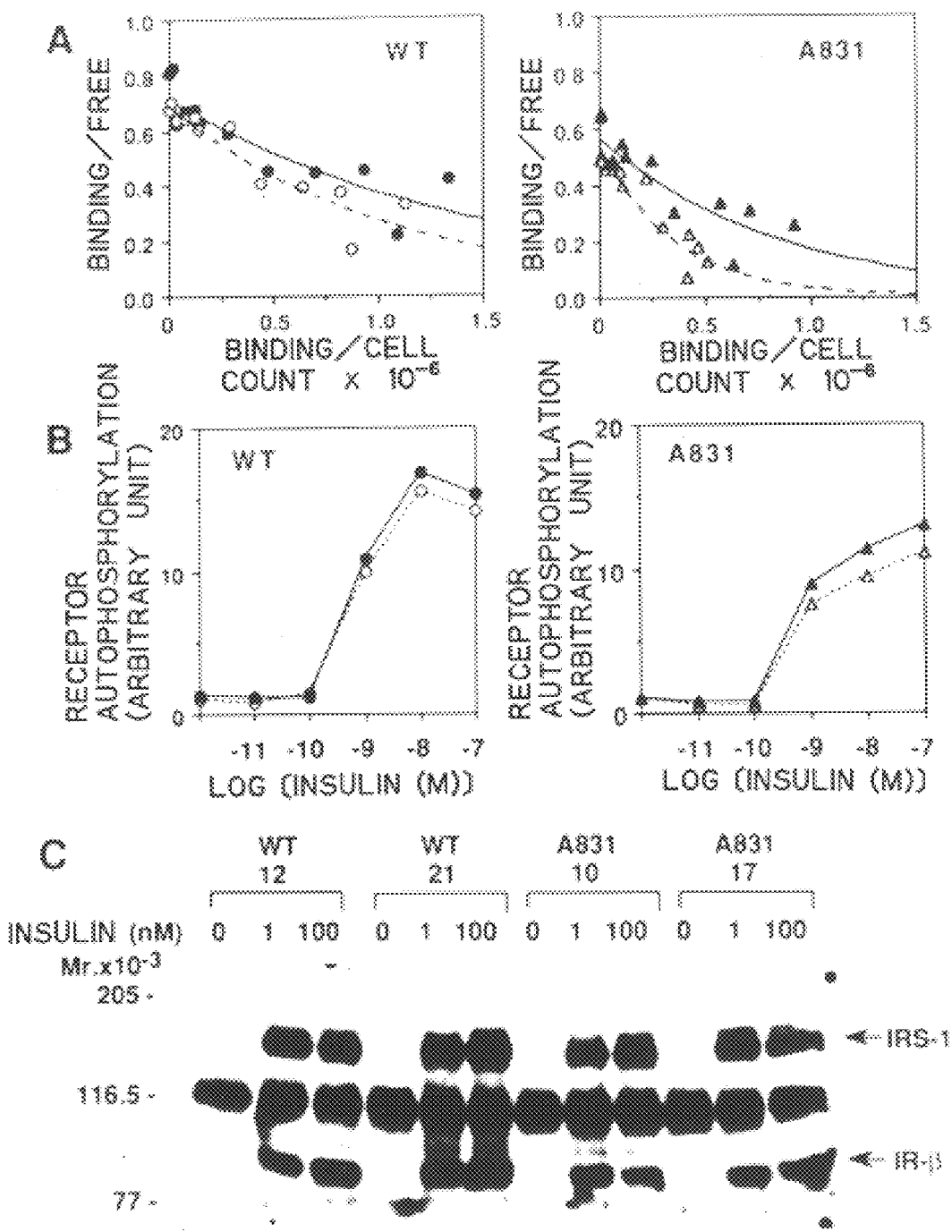
FIG. 3 shows insulin binding (A) and receptor tyrosine kinase activity (B,C) of wild type ($IR^{WT}$) and the mutant ($IR^{A831}$) receptors. (A) Confluent CHO cells expressing $IR^{WT}$ (clone No. 12: ○ - - - ○, clone No. 21: ○ - - - ○) or $IR^{A831}$ (clone No. 10: Δ - - - Δ, clone No. 17: Δ - - - Δ) were incubated with $^{125}I$-insulin of various concentrations at 4° C. for 12 hours. The radioactivity of the bound $^{125}I$-insulin was measured and plotted in accordance with the method of Scatchard. (B) Insulin-dependent receptor autophosphorylating activity was shown as the amount of $^{32}P$ incorporated into the insulin receptor β-subunit with the use of the same cell lines as those employed in (A). (C) An electrophorogram of the immunoblotting of insulin-dependent tyrosine phosphorylations of IRS-1 and IR β-subunits measured with an anti-phospho-tyrosine antibody with the use of the same cell lines as those employed in (A).

FIG. 3A shows the Scatchard analysis of IR$^{WT}$ (clone Nos. 12 and 21) and IR$^{A831}$ (clone Nos. 10 and 17). The number of insulin binding sites in each clone were counted. As a result, the number of high affinity binding sites were 1.1 and a.5×10$^6$ per cell in IR$^{WT}$ and 0.5 and 0.9×10$^9$ per cell in IR$^{A831}$, and the dissociation constants (Kd) were 2.8 and 3.5 nM for IR$^{WT}$ and 1.7 and 2.7 nM for IR$^{A831}$. IR$^{WT}$ and IR$^{A831}$ showed each the occurrence of dissociation with a decrease in pH (from 7.5 to 5.5) and no difference was observed between the wild type and the mutant IRs.

Next, the autophosphorylation activities of these receptors were determined by the test method (3) described above.

FIG. 3B shows the results thus obtained. As FIG. 3B clearly shows, the activities of receptor autophosphorylation were increased in association with the receptor numbers. Half-maximal stimulation occurred at 5.5 and 5.4×10⁻¹⁰ M for $IR^{WT}$ and at 5.0 and 4.9×10⁻¹⁰ for $IR^{A831}$, showing no remarkable difference between the wild type and the mutant IRs.

Further, the tyrosine kinase activity toward an endogenous substrate IRS-1 was determined by immunoblotting with the use of an anti-phosphotyrosine antibody (PY-20). FIG. 3C shows the results. As FIG. 3C clearly shows, the IRS-1 (molecular weight: 160,000) was phosphorylated insulin-dependently at tyrosine residues in parallel to the autophosphorylation rate of the receptor β-subunit (molecular weight: 95,000).

Subsequently, the insulin binding and receptor autophosphorylation were examined by using COS cells transiently expressing $IR^{WT}$ and $IR^{A831}$ so as to avoid differences among CHO clones stably expressing each IR. No remarkable difference was observed between the wild type and artificial mutant receptors in either insulin binding affinity or in receptor kinase activity. Similarly, no distinct difference was observed between the wild type and artificial mutant receptors in receptor processing, internalization, degradation, insulin-stimulated glucose uptake, glycogen synthesis and DNA synthesis. That is to say, no direct evidence was found regarding the receptor function disorders in the A831 mutation.

(2) C1334 mutation

The above-mentioned experiments performed on $IR^{A831}$ were repeated on $IR^{C1334}$ to thereby examine the receptor function disorders in $IR^{C1334}$.

No distinct difference in the functions between $IR^{C1334}$ and $RI^{WT}$ was found out in the examination with the use of CHO clones stably expressing IRs.

However, a difference was observed in the affinity to PI 3-kinase. It is known that the autophosphorylated $Tyr^{1334}$ of IR locates in the putative binding motif [Y(P)XXM] to the SH2 domains of the 85-kDa regulatory subunit (p85) of phosphatidylinositol 3-kinase (D. J. Van Horn et al., J. Biol. Chem. 269:29–32, 1994). Since the binding of autophosphorylated IR to PI 3-kinase in response to insulin leads to the activation of this enzyme, this mechanism might be an alternative pathway for the activation of PI 3-kinase by the binding of IRS-1. The present inventors had formerly reported that PI 3-kinase mediates the translocation of glucose transporter type 4 (GLUT4) (see, for example, F. Kanai et al., Biochem. Biophys. Res. Commun. 195:762–768, 1993). Thus examination was made on the direct interactions between $IR^{C1334}$ and p85 of PI 3-kinase.

Figure 4:
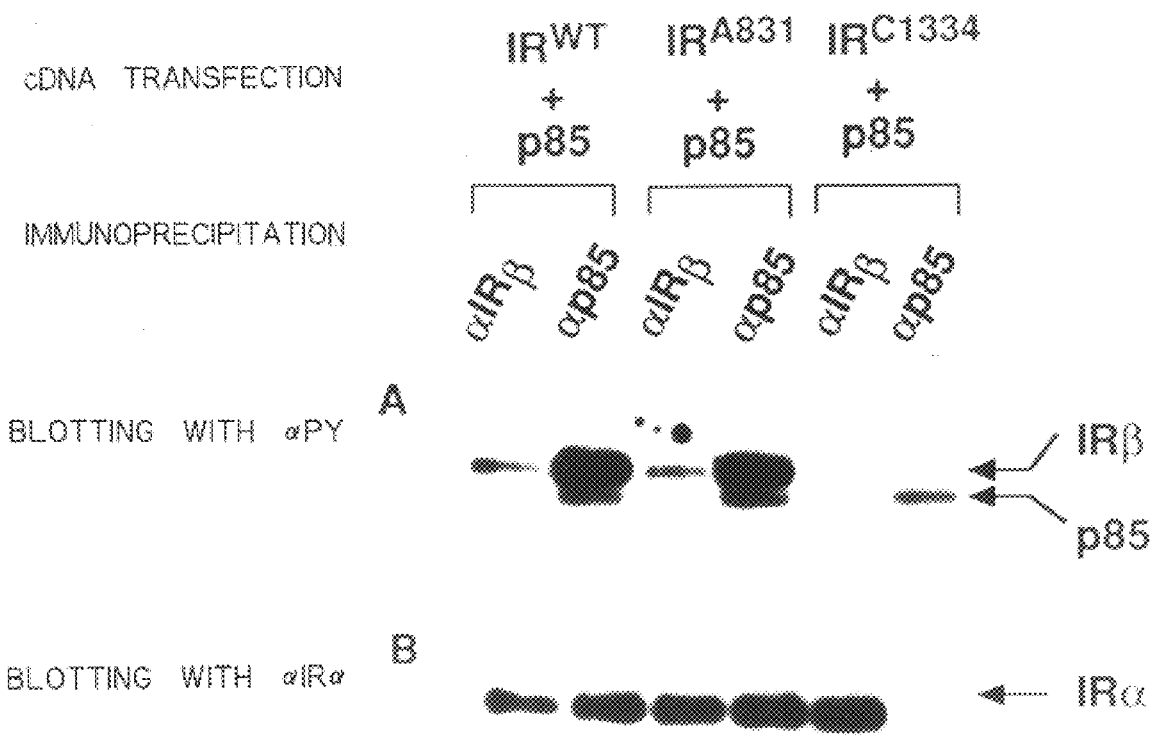
FIG. 4 shows insulin-induced complex formation of the normal insulin receptor and two artificially mutated insulin receptors ($IR^{A831}$ and $IR^{C1334}$) and the p85 subunit of PI 3-kinase. The p85 subunit of PI 3-kinase was transiently co-expressed with the wild type IR ($IR^{WT}$) or the mutant IRs ($IR^{A831}$ and $IR^{C1334}$) in COS cells, respectively. In the presence of $10^{-7}$ M of insulin, the cell lysates were immunoprecipitated by an anti-β-subunit of IR (α-IRβ) or anti-p85 (αp85) antibodies. (A) and (B) are electrophorograms obtained by immunoblotting the immunoprecipitates with (A) an anti-phosphotyrosine antibody (αPY) or (B) an anti-α-subunit of IR antibody (αIRα).

First, the p85 subunit of PI 3-kinase was transiently expressed in COS cells with the use of $IR^{WT}$, $IR^{A831}$ and $IR^{C1334}$. After treating with insulin, the cell lysates were precipitated by either an anti-IRβ antibody (αIRβ) or an anti-p85 antibody (αp85) (FIG. 4). The immunoprecipitates were examined by immunoblotting with an anti-phosphotyrosine antibody (αPY) (FIG. 4A) or an anti-IR α-subunit antibody (αIRα) (FIG. 4B). In the transient expression system, the insulin treatment stimulated the tyrosine phosphorylation of the p85 subunit of PI 3-kinase and the binding of the p85 to $IR^{WT}$. When immunoblotted with anti-IRα antibody, the anti-IRβ antibody precipitated $IR^{WT,IR}$A831 and $IR^{C1334}$ to almost the same degree (FIG. 4B). When immunoblotted with anti-p85 antibody, the anti-p85 antibody precipitated $IR^{WT}$, $IR^{A831}$ and $IR^{C1334}$ to almost the same degree.

Subsequently, examination was made on the tyrosine phosphorylation of p85 and IRβ, and the binding of p85 to $IR^{WT}$, $IR^{A831}$ and $IR^{C1334}$. When immunoblotted with anti-phosphotyrosine antibody (FIG. 4A), all of the IRs phosphorylated p85 at tyrosine residues to the same extent. The tyrosine phosphorylation of $IR^{C1334}$ was reduced compared with $IR^{WT}$ and $IR^{A831}$ (FIG. 4A). This reduction did not relate to the decrease in the tyrosine kinase activity of $IR^{C1334}$. In the examination on the incorporation of ³²P into the substrates, $IR^{C1334}$ showed almost the same activity toward the autophosphorylation sites and an exogenous substrate poly(Glu, Tyr) 4:1 as $IR^{WT}$ and $IR^{A831}$ in CHO cells expressing these IRs. Thus it is considered that the antiphosphotyrosine antibody would preferably recognize the site of autophosphorylated $Y^{1334}$ more than other autophosphorylation sites of IRβ. The anti-p85 antibody co-precipitated with $IR^{WT}$ and $IR^{A831}$ but not with $IR^{C1334}$ (FIG. 4B). This fact means that $IR^{C1334}$ would not bind to p85 and that the major binding site of IR to p85 might be the $Y^{1334}$ residue.

Example 5

Statistical Processing 272 healthy volunteers were analyzed to find those having the mutant insulin receptor DNA ($Thr^{831} \rightarrow Ala^{831}$). As a result, none of the volunteers showed the mutation. Thus, the relation between the mutant insulin receptor DNA of the present invention and NIDDM was tested through statistical processing by chi-square analysis. The results are given in the following Table 1.

TABLE 1

Analysis on the frequency of the occurrence of insulin receptor β-subunit mutation ($T^{831} \rightarrow A^{831}$) in NIDDM and non-diabetic subjects

|  | NIDDM | Non-diabetic[1] | Total |
|---|---|---|---|
| $A^{831}$ | 3[2] | 0 | 3 |
| $T^{831}$ | 48 | 272 | 320 |
| Total | 51 | 272 | 323 |

[1]The non-diabetic subjects were not examined by OGTT, etc. but selected by inquiring whether they had any medical history or family histories of diabetes in their immediate parents or grandparents.
[2]The mutation ($Thr^{831} \rightarrow Ala^{831}$) significantly related to the onset of NIDDM in the chi-square analysis with Yates correction (p < 0.05). Supposing that the spontaneous onset rate of NIDDM is 5% and 5% (14 subjects) of the 272 non-diabetic subjects might migrate into the NIDDM $T^{831}$ group, the mutation still shows a significant difference in the above calibration.

Example 6

Pedigree-linkage Analysis (1) Relationship between $IR^{C133}$ and the onset of NIDDM To examine the relationship between $IR^{C1334}$ and the onset of NIDDM, data on the family with $IR^{C1334}$ were analyzed.

Figure 5:
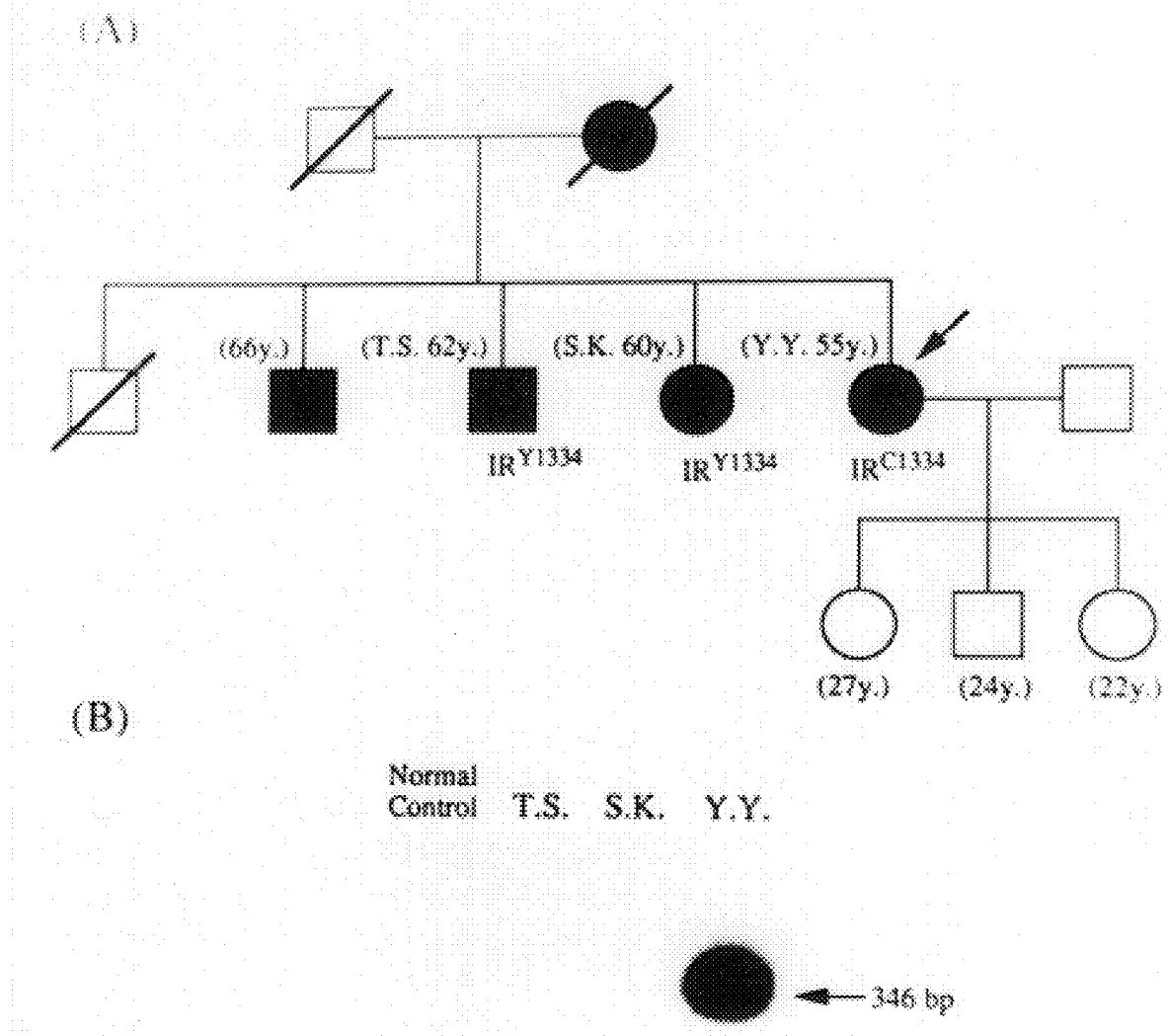
FIG. 5 shows analysis on the relationship between the mutation and the onset of NIDDM in a pedigree with the mutant $IR^{C1334}$. (A) Familial analysis of TAC ($Tyr^{1334}$)→TGC ($Cys^{1334}$) replacement. Squares and circles stand respectively for male and female. Closed symbols stand for patients with NIDDM, the arrow shows the proband and slashed symbols stand for deceased. (B) Allele-specific hybridization. PCR products originating from the insulin receptor exon 22 of the genomic DNAs of three patients and a normal subject were separated in an agarose gel and transferred onto a nitrocellulose filter. After hybridizing with a $^{32}P$-labeled oligonucleotide probe specific to the mutant allele, the filter was autoradio-graphed. The $IR^{C1334}$ mutation (a 346 bp fragment) was identified in one allele of the proband (Y. Y.) but not in a brother (T. S.) and a sister (S. K.).

In this family, the mother and the second son were reported to be diabetics, and the other two children (T. S. and S. K.) in addition to the proband (Y. Y.) were diagnosed as diabetics (FIG. 5A). When examined by the allele specific hybridization at TAC ($Tyr^{1334}$)→TGC ($Cys^{1334}$) (FIG. 5B), however, two of them (T. S. and S. K.) had the normal IR ($IR^{Y1334}$) while the proband alone had $IR^{C1334}$. Thus the results of this pedigree-linkage analysis indicate that the mutant $IR^{C1334}$ is not the common cause of the onset of NIDDM in this family.

(2) Relationship between $IR^{A831}$ and the onset of NIDDM

Figure 6:
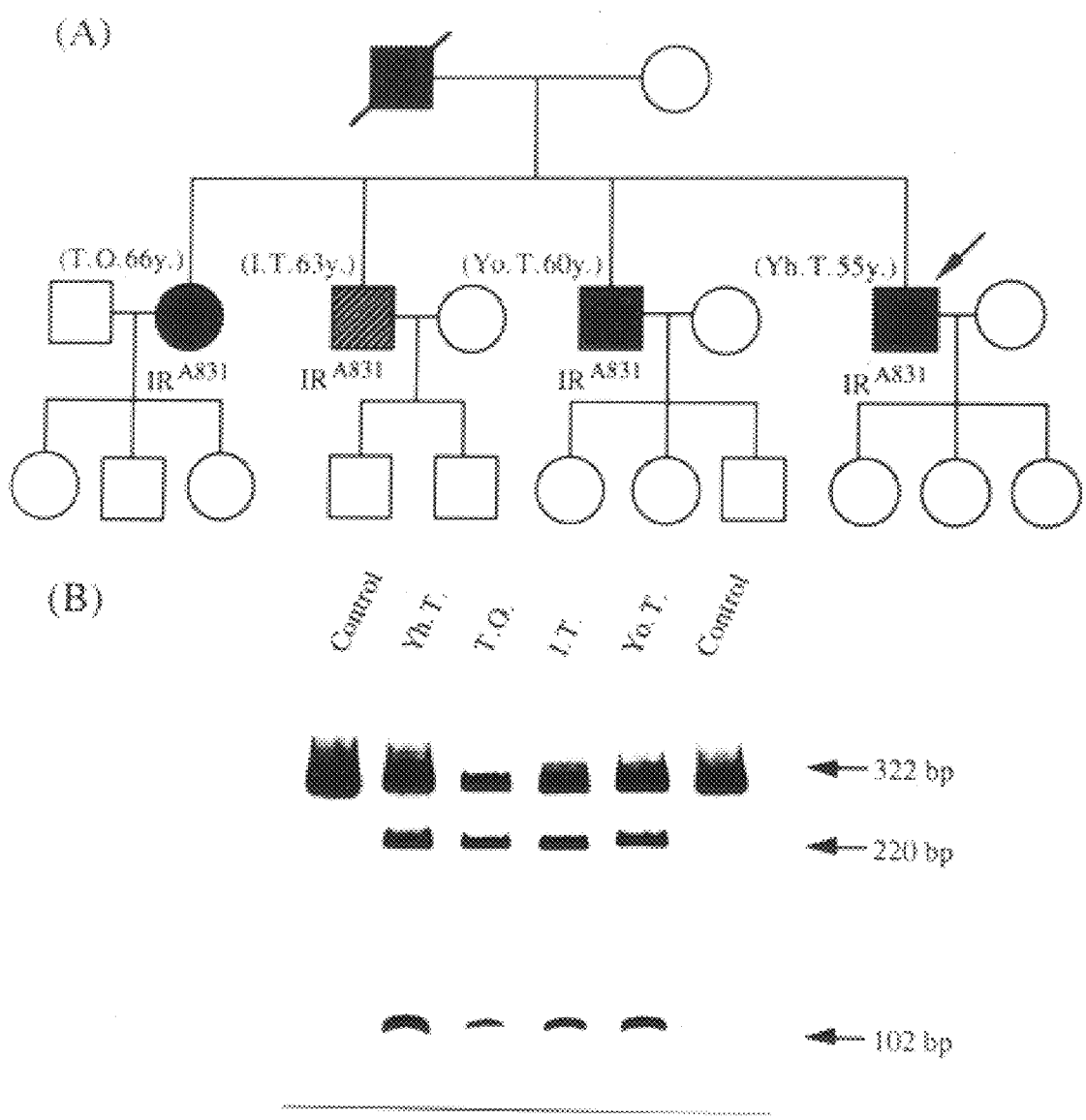
FIG. 6 shows an analysis of the relationship between the mutation and the onset of NIDDM in a pedigree with the mutant $IR^{A831}$. (A) Familial analysis of ACG (Thr$^{831}$)→GCG (Ala$^{831}$) replacement. The IR$^{A831}$ mutation was identified in one allele of the proband (Yh. T.), two brothers (I. T. and Yo. T.) and a sister (T. O.). The arrow shows the proband, squares and circles stand respectively for male and female. Closed symbols stand for patients with NIDDM, shaded symbols stand for IGT (impaired glucose tolerance) and slashed symbols stand for deceased. (B) An electrophorogram showing the detection of IR$^{A831}$ by the restriction enzyme digestion. The IR$^{A831}$ mutation in the PCR fragment of the exon 13 cleaved a cleavage site specific for the restriction enzyme CfoI. The CfoI-digestion product of the mutated PCR fragment (332 bp) resulted in the appearance of two bands (102 bp and 220 bp), while this cleavage was prevented in the wild type.

To examine the relationship between $IR^{A831}$ and the onset of NIDDM, data on the family with $IR^{A831}$ were analyzed. The deceased proband's father had NIDDM, but his mutation could not be confirmed. The mother could not be subjected to the examination due to her advanced age. All four siblings were heterozygotes of IR$^{A831}$, and three had NIDDM while one had an impaired glucose tolerance (IGT), i.e., intermediate between normal and diabetes (FIG. 6). IR$^{A831}$ was detected by the above-mentioned method with the formation of the specific cleavage site of the restriction enzyme CfoI (FIG. 6B). Consanguineous marriage in the family was ruled out. The allele of IR$^{A831}$ may have been derived from the father. This pedigree and linkage analysis data strongly suggest that the heterozygous mutation IR$^{A831}$ would be responsible for the onset of NIDDM.

---

I claim:

1. A mutant human insulin receptor DNA, wherein the base sequence encoding $Thr^{831}$ in human insulin receptor DNA has been replaced by a base sequence encoding Ala and/or the base sequence encoding $Tyr^{1334}$ therein has been replaced by a base sequence encoding Cys, or a fragment of said mutant human insulin receptor DNA containing the mutation, comprising the base sequence encoding Ala and/or the base sequence encoding Cys.

2. The mutant human insulin receptor DNA as claimed in claim 1, wherein the base sequence (ACG) encoding $Thr^{831}$ in the exon 13 of the β-subunit in human insulin receptor DNA has been replaced by a base sequence (GCG) encoding Ala, or a fragment of the same containing the mutation.

3. The mutant human insulin receptor DNA as claimed in claim 1, wherein the base sequence (TAC) encoding $Tyr^{1334}$ in the exon 22 of the β-subunit in human insulin receptor DNA has been replaced by a base sequence (TGC) encoding Cys, or a fragment of the same containing the mutation.

4. The mutant human insulin receptor DNA as claimed in claim 1 which does not bind to phosphatidylinositol 3-kinase or a fragment of the same containing the mutation.

5. The DNA which is complementary to a mutant human insulin receptor DNA as claimed in claim 1 or a fragment of the same containing the mutation.

6. A diagnostic probe for non-insulin-dependent diabetes mellitus which comprises a mutant human insulin receptor fragment as claimed in any one of claims 1 to 5.

7. A diagnostic drug for non-insulin-dependent diabetes mellitus which contains a mutant human insulin receptor fragment as claimed in any one of claims 1 to 5.

8. The probe of claim 6, wherein said fragment comprises from 10 to 50 bases.

9. A method for diagnosing non-insulin-dependent diabetes mellitus, comprising the steps of:
   (a) amplifying a DNA region containing the base sequence encoding $Thr^{831}$ and/or $Tyr^{1334}$ in human insulin receptor DNA from a nucleic acid sample obtained from a subject; and
   (b) detecting a mutation of the base sequence in said DNA region, wherein the mutation is such that the base sequence encoding $Thr^{831}$ has been replaced by a base sequence encoding Ala and/or the base sequence encoding $Tyr^{1334}$ has been replaced by a base sequence encoding Cys and wherein the mutation is diagnostic for non-insulin-dependent diabetes mellitus.

10. The method of claim 9, wherein the method for detecting the mutation is a restriction fragment length polymorphism (RFLP) method.

11. The method of claim 9, wherein the method for detecting the mutation is allele-specific hybridization method.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 4149 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..4146

(ix) FEATURE:
        (A) NAME/KEY: mat_peptide
        (B) LOCATION: 82..4146

(xi) SEQUENCE DESCRIPTION: SEQ ID NO:1:

```
ATG GGC ACC GGG GGC CGG CGG GGG GCG GCG GCC GCG CCG CTG CTG GTG        48
Met Gly Thr Gly Gly Arg Arg Gly Ala Ala Ala Ala Pro Leu Leu Val
-27     -25                 -20                 -15

GCG GTG GCC GCG CTG CTA CTG GGC GCC GCG GGC CAC CTG TAC CCC GGA        96
Ala Val Ala Ala Leu Leu Leu Gly Ala Ala Gly His Leu Tyr Pro Gly
    -10                  -5                   1              5

GAG GTG TGT CCC GGC ATG GAT ATC CGG AAC AAC CTC ACT AGG TTG CAT       144
Glu Val Cys Pro Gly Met Asp Ile Arg Asn Asn Leu Thr Arg Leu His
                10                  15                  20

GAG CTG GAG AAT TGC TCT GTC ATC GAA GGA CAC TTG CAG ATA CTC TTG       192
Glu Leu Glu Asn Cys Ser Val Ile Glu Gly His Leu Gln Ile Leu Leu
                25                  30                  35

ATG TTC AAA ACG AGG CCC GAA GAC TTC CGA GAC CTC AGT TTC CCC AAA       240
Met Phe Lys Thr Arg Pro Glu Asp Phe Arg Asp Leu Ser Phe Pro Lys
            40                  45                  50

CTC ATC ATG ATC ACT GAT TAC TTG CTG CTC TTC CGG GTC TAT GGG CTC       288
Leu Ile Met Ile Thr Asp Tyr Leu Leu Leu Phe Arg Val Tyr Gly Leu
        55                  60                  65

GAG AGC CTG AAG GAC CTG TTC CCC AAC CTC ACG GTC ATC CGG GGA TCA       336
Glu Ser Leu Lys Asp Leu Phe Pro Asn Leu Thr Val Ile Arg Gly Ser
70                  75                  80                  85

CGA CTG TTC TTT AAC TAC GCG CTG GTC ATC TTC GAG ATG GTT CAC CTC       384
Arg Leu Phe Phe Asn Tyr Ala Leu Val Ile Phe Glu Met Val His Leu
                90                  95                 100

AAG GAA CTC GGC CTC TAC AAC CTG ATG AAC ATC ACC CGG GGT TCT GTC       432
Lys Glu Leu Gly Leu Tyr Asn Leu Met Asn Ile Thr Arg Gly Ser Val
            105                 110                 115

CGC ATC GAG AAG AAC AAT GAG CTC TGT TAC TTG GCC ACT ATC GAC TGG       480
Arg Ile Glu Lys Asn Asn Glu Leu Cys Tyr Leu Ala Thr Ile Asp Trp
        120                 125                 130

TCC CGT ATC CTG GAT TCC GTG GAG GAT AAT CAC ATC GTG TTG AAC AAA       528
Ser Arg Ile Leu Asp Ser Val Glu Asp Asn His Ile Val Leu Asn Lys
135                 140                 145
```

```
GAT GAC AAC GAG GAG TGT GGA GAC ATC TGT CCG GGT ACC GCG AAG GGC         576
Asp Asp Asn Glu Glu Cys Gly Asp Ile Cys Pro Gly Thr Ala Lys Gly
150                 155                 160                 165

AAG ACC AAC TGC CCC GCC ACC GTC ATC AAC GGG CAG TTT GTC GAA CGA         624
Lys Thr Asn Cys Pro Ala Thr Val Ile Asn Gly Gln Phe Val Glu Arg
                170                 175                 180

TGT TGG ACT CAT AGT CAC TGC CAG AAA GTT TGC CCG ACC ATC TGT AAG         672
Cys Trp Thr His Ser His Cys Gln Lys Val Cys Pro Thr Ile Cys Lys
                    185                 190                 195

TCA CAC GGC TGC ACC GCC GAA GGC CTC TGT TGC CAC AGC GAG TGC CTG         720
Ser His Gly Cys Thr Ala Glu Gly Leu Cys Cys His Ser Glu Cys Leu
                        200                 205                 210

GGC AAC TGT TCT CAG CCC GAC GAC CCC ACC AAG TGC GTG GCC TGC CGC         768
Gly Asn Cys Ser Gln Pro Asp Asp Pro Thr Lys Cys Val Ala Cys Arg
                            215                 220                 225

AAC TTC TAC CTG GAC GGC AGG TGT GTG GAG ACC TGC CCG CCC CCG TAC         816
Asn Phe Tyr Leu Asp Gly Arg Cys Val Glu Thr Cys Pro Pro Pro Tyr
230                 235                 240                 245

TAC CAC TTC CAG GAC TGG CGC TGT GTG AAC TTC AGC TTC TGC CAG GAC         864
Tyr His Phe Gln Asp Trp Arg Cys Val Asn Phe Ser Phe Cys Gln Asp
                    250                 255                 260

CTG CAC CAC AAA TGC AAG AAC TCG CGG AGG CAG GGC TGC CAC CAA TAC         912
Leu His His Lys Cys Lys Asn Ser Arg Arg Gln Gly Cys His Gln Tyr
                        265                 270                 275

GTC ATT CAC AAC AAC AAG TGC ATC CCT GAG TGT CCC TCC GGG TAC ACG         960
Val Ile His Asn Asn Lys Cys Ile Pro Glu Cys Pro Ser Gly Tyr Thr
                            280                 285                 290

ATG AAT TCC AGC AAC TTG CTG TGC ACC CCA TGC CTG GGT CCC TGT CCC        1008
Met Asn Ser Ser Asn Leu Leu Cys Thr Pro Cys Leu Gly Pro Cys Pro
                                295                 300                 305

AAG GTG TGC CAC CTC CTA GAA GGC GAG AAG ACC ATC GAC TCG GTG ACG        1056
Lys Val Cys His Leu Leu Glu Gly Glu Lys Thr Ile Asp Ser Val Thr
310                 315                 320                 325

TCT GCC CAG GAG CTC CGA GGA TGC ACC GTC ATC AAC GGG AGT CTG ATC        1104
Ser Ala Gln Glu Leu Arg Gly Cys Thr Val Ile Asn Gly Ser Leu Ile
                    330                 335                 340

ATC AAC ATT CGA GGA GGC AAC AAT CTG GCA GCT GAG CTA GAA GCC AAC        1152
Ile Asn Ile Arg Gly Gly Asn Asn Leu Ala Ala Glu Leu Glu Ala Asn
                        345                 350                 355

CTC GGC CTC ATT GAA GAA ATT TCA GGG TAT CTA AAA ATC CGC CGA TCC        1200
Leu Gly Leu Ile Glu Glu Ile Ser Gly Tyr Leu Lys Ile Arg Arg Ser
                            360                 365                 370

TAC GCT CTG GTG TCA CTT TCC TTC TTC CGG AAG TTA CGT CTG ATT CGA        1248
Tyr Ala Leu Val Ser Leu Ser Phe Phe Arg Lys Leu Arg Leu Ile Arg
                                375                 380                 385

GGA GAG ACC TTG GAA ATT GGG AAC TAC TCC TTC TAT GCC TTG GAC AAC        1296
Gly Glu Thr Leu Glu Ile Gly Asn Tyr Ser Phe Tyr Ala Leu Asp Asn
390                 395                 400                 405

CAG AAC CTA AGG CAG CTC TGG GAC TGG AGC AAA CAC AAC CTC ACC ACC        1344
Gln Asn Leu Arg Gln Leu Trp Asp Trp Ser Lys His Asn Leu Thr Thr
                    410                 415                 420

ACT CAG GGG AAA CTC TTC TTC CAC TAT AAC CCC AAA CTC TGC TTG TCA        1392
Thr Gln Gly Lys Leu Phe Phe His Tyr Asn Pro Lys Leu Cys Leu Ser
                        425                 430                 435

GAA ATC CAC AAG ATG GAA GAA GTT TCA GGA ACC AAG GGG CGC CAG GAG        1440
Glu Ile His Lys Met Glu Glu Val Ser Gly Thr Lys Gly Arg Gln Glu
                            440                 445                 450

AGA AAC GAC ATT GCC CTG AAG ACC AAT GGG GAC AAG GCA TCC TGT GAA        1488
Arg Asn Asp Ile Ala Leu Lys Thr Asn Gly Asp Lys Ala Ser Cys Glu
                                455                 460                 465
```

-continued

| | |
|---|---|
| AAT GAG TTA CTT AAA TTT TCT TAC ATT CGG ACA TCT TTT GAC AAG ATC<br>Asn Glu Leu Leu Lys Phe Ser Tyr Ile Arg Thr Ser Phe Asp Lys Ile<br>470                     475                    480                   485 | 1536 |
| TTG CTG AGA TGG GAG CCG TAC TGG CCC CCC GAC TTC CGA GAC CTC TTG<br>Leu Leu Arg Trp Glu Pro Tyr Trp Pro Pro Asp Phe Arg Asp Leu Leu<br>                    490                    495                   500 | 1584 |
| GGG TTC ATG CTG TTC TAC AAA GAG GCC CCT TAT CAG AAT GTG ACG GAG<br>Gly Phe Met Leu Phe Tyr Lys Glu Ala Pro Tyr Gln Asn Val Thr Glu<br>               505                    510                   515 | 1632 |
| TTC GAT GGG CAG GAT GCG TGT GGT TCC AAC AGT TGG ACG GTG GTA GAC<br>Phe Asp Gly Gln Asp Ala Cys Gly Ser Asn Ser Trp Thr Val Val Asp<br>     520                    525                   530 | 1680 |
| ATT GAC CCA CCC CTG AGG TCC AAC GAC CCC AAA TCA CAG AAC CAC CCA<br>Ile Asp Pro Pro Leu Arg Ser Asn Asp Pro Lys Ser Gln Asn His Pro<br>535                     540                    545 | 1728 |
| GGG TGG CTG ATG CGG GGT CTC AAG CCC TGG ACC CAG TAT GCC ATC TTT<br>Gly Trp Leu Met Arg Gly Leu Lys Pro Trp Thr Gln Tyr Ala Ile Phe<br>550                     555                    560               565 | 1776 |
| GTG AAG ACC CTG GTC ACC TTT TCG GAT GAA CGC CGG ACC TAT GGG GCC<br>Val Lys Thr Leu Val Thr Phe Ser Asp Glu Arg Arg Thr Tyr Gly Ala<br>               570                    575                   580 | 1824 |
| AAG AGT GAC ATC ATT TAT GTC CAG ACA GAT GCC ACC AAC CCC TCT GTG<br>Lys Ser Asp Ile Ile Tyr Val Gln Thr Asp Ala Thr Asn Pro Ser Val<br>     585                    590                   595 | 1872 |
| CCC CTG GAT CCA ATC TCA GTG TCT AAC TCA TCA TCC CAG ATT ATT CTG<br>Pro Leu Asp Pro Ile Ser Val Ser Asn Ser Ser Ser Gln Ile Ile Leu<br>600                     605                    610 | 1920 |
| AAG TGG AAA CCA CCC TCC GAC CCC AAT GGC AAC ATC ACC CAC TAC CTG<br>Lys Trp Lys Pro Pro Ser Asp Pro Asn Gly Asn Ile Thr His Tyr Leu<br>     615                    620                   625 | 1968 |
| GTT TTC TGG GAG AGG CAG GCG GAA GAC AGT GAG CTG TTC GAG CTG GAT<br>Val Phe Trp Glu Arg Gln Ala Glu Asp Ser Glu Leu Phe Glu Leu Asp<br>630                     635                    640               645 | 2016 |
| TAT TGC CTC AAA GGG CTG AAG CTG CCC TCG AGG ACC TGG TCT CCA CCA<br>Tyr Cys Leu Lys Gly Leu Lys Leu Pro Ser Arg Thr Trp Ser Pro Pro<br>               650                    655                   660 | 2064 |
| TTC GAG TCT GAA GAT TCT CAG AAG CAC AAC CAG AGT GAG TAT GAG GAT<br>Phe Glu Ser Glu Asp Ser Gln Lys His Asn Gln Ser Glu Tyr Glu Asp<br>               665                    670                   675 | 2112 |
| TCG GCC GGC GAA TGC TGC TCC TGT CCA AAG ACA GAC TCT CAG ATC CTG<br>Ser Ala Gly Glu Cys Cys Ser Cys Pro Lys Thr Asp Ser Gln Ile Leu<br>     680                    685                   690 | 2160 |
| AAG GAG CTG GAG GAG TCC TCG TTT AGG AAG ACG TTT GAG GAT TAC CTG<br>Lys Glu Leu Glu Glu Ser Ser Phe Arg Lys Thr Phe Glu Asp Tyr Leu<br>695                     700                    705 | 2208 |
| CAC AAC GTG GTT TTC GTC CCC AGA AAA ACC TCT TCA GGC ACT GGT GCC<br>His Asn Val Val Phe Val Pro Arg Lys Thr Ser Ser Gly Thr Gly Ala<br>710                     715                    720               725 | 2256 |
| GAG GAC CCT AGG CCA TCT CGG AAA CGC AGG TCC CTT GGC GAT GTT GGG<br>Glu Asp Pro Arg Pro Ser Arg Lys Arg Arg Ser Leu Gly Asp Val Gly<br>               730                    735                   740 | 2304 |
| AAT GTG ACG GTG GCC GTG CCC ACG GTG GCA GCT TTC CCC AAC ACT TCC<br>Asn Val Thr Val Ala Val Pro Thr Val Ala Ala Phe Pro Asn Thr Ser<br>               745                    750                   755 | 2352 |
| TCG ACC AGC GTG CCC ACG AGT CCG GAG GAG CAC AGG CCT TTT GAG AAG<br>Ser Thr Ser Val Pro Thr Ser Pro Glu Glu His Arg Pro Phe Glu Lys<br>     760                    765                   770 | 2400 |
| GTG GTG AAC AAG GAG TCG CTG GTC ATC TCC GGC TTG CGA CAC TTC ACG<br>Val Val Asn Lys Glu Ser Leu Val Ile Ser Gly Leu Arg His Phe Thr<br>775                     780                    785 | 2448 |

-continued

| | |
|---|---|
| GGC TAT CGC ATC GAG CTG CAG GCT TGC AAC CAG GAC ACC CCT GAG GAA<br>Gly Tyr Arg Ile Glu Leu Gln Ala Cys Asn Gln Asp Thr Pro Glu Glu<br>790                     795                   800                  805 | 2496 |
| CGG TGC AGT GTG GCA GCC TAC GTC AGT GCG AGG ACC ATG CCT GAA GCC<br>Arg Cys Ser Val Ala Ala Tyr Val Ser Ala Arg Thr Met Pro Glu Ala<br>                   810                   815                   820 | 2544 |
| AAG GCT GAT GAC ATT GTT GGC CCT GTG ACG CAT GAA ATC TTT GAG AAC<br>Lys Ala Asp Asp Ile Val Gly Pro Val Thr His Glu Ile Phe Glu Asn<br>            825                   830                   835 | 2592 |
| AAC GTC GTC CAC TTG ATG TGG CAG GAG CCG AAG GAG CCC AAT GGT CTG<br>Asn Val Val His Leu Met Trp Gln Glu Pro Lys Glu Pro Asn Gly Leu<br>           840                   845                   850 | 2640 |
| ATC GTG CTG TAT GAA GTG AGT TAT CGG CGA TAT GGT GAT GAG GAG CTG<br>Ile Val Leu Tyr Glu Val Ser Tyr Arg Arg Tyr Gly Asp Glu Glu Leu<br>855                     860                   865 | 2688 |
| CAT CTC TGC GTC TCC CGC AAG CAC TTC GCT CTG GAA CGG GGC TGC AGG<br>His Leu Cys Val Ser Arg Lys His Phe Ala Leu Glu Arg Gly Cys Arg<br>870                     875                   880                   885 | 2736 |
| CTG CGT GGG CTG TCA CCG GGG AAC TAC AGC GTG CGA ATC CGG GCC ACC<br>Leu Arg Gly Leu Ser Pro Gly Asn Tyr Ser Val Arg Ile Arg Ala Thr<br>           890                   895                   900 | 2784 |
| TCC CTT GCG GGC AAC GGC TCT TGG ACG GAA CCC ACC TAT TTC TAC GTG<br>Ser Leu Ala Gly Asn Gly Ser Trp Thr Glu Pro Thr Tyr Phe Tyr Val<br>                   905                   910                   915 | 2832 |
| ACA GAC TAT TTA GAC GTC CCG TCA AAT ATT GCA AAA ATT ATC ATC GGC<br>Thr Asp Tyr Leu Asp Val Pro Ser Asn Ile Ala Lys Ile Ile Ile Gly<br>           920                   925                   930 | 2880 |
| CCC CTC ATC TTT GTC TTT CTC TTC AGT GTT GTG ATT GGA AGT ATT TAT<br>Pro Leu Ile Phe Val Phe Leu Phe Ser Val Val Ile Gly Ser Ile Tyr<br>935                     940                   945 | 2928 |
| CTA TTC CTG AGA AAG AGG CAG CCA GAT GGG CCG CTG GGA CCG CTT TAC<br>Leu Phe Leu Arg Lys Arg Gln Pro Asp Gly Pro Leu Gly Pro Leu Tyr<br>950                     955                   960                   965 | 2976 |
| GCT TCT TCA AAC CCT GAG TAT CTC AGT GCC AGT GAT GTG TTT CCA TGC<br>Ala Ser Ser Asn Pro Glu Tyr Leu Ser Ala Ser Asp Val Phe Pro Cys<br>           970                   975                   980 | 3024 |
| TCT GTG TAC GTG CCG GAC GAG TGG GAG GTG TCT CGA GAG AAG ATC ACC<br>Ser Val Tyr Val Pro Asp Glu Trp Glu Val Ser Arg Glu Lys Ile Thr<br>                   985                   990                   995 | 3072 |
| CTC CTT CGA GAG CTG GGG CAG GGC TCC TTC GGC ATG GTG TAT GAG GGC<br>Leu Leu Arg Glu Leu Gly Gln Gly Ser Phe Gly Met Val Tyr Glu Gly<br>          1000                  1005                 1010 | 3120 |
| AAT GCC AGG GAC ATC ATC AAG GGT GAG GCA GAG ACC CGC GTG GCG GTG<br>Asn Ala Arg Asp Ile Ile Lys Gly Glu Ala Glu Thr Arg Val Ala Val<br>          1015                  1020                 1025 | 3168 |
| AAG ACG GTC AAC GAG TCA GCC AGT CTC CGA GAG CGG ATT GAG TTC CTC<br>Lys Thr Val Asn Glu Ser Ala Ser Leu Arg Glu Arg Ile Glu Phe Leu<br>1030                    1035                  1040                 1045 | 3216 |
| AAT GAG GCC TCG GTC ATG AAG GGC TTC ACC TGC CAT CAC GTG GTG CGC<br>Asn Glu Ala Ser Val Met Lys Gly Phe Thr Cys His His Val Val Arg<br>          1050                  1055                 1060 | 3264 |
| CTC CTG GGA GTG GTG TCC AAG GGC CAG CCC ACG CTG GTG GTG ATG GAG<br>Leu Leu Gly Val Val Ser Lys Gly Gln Pro Thr Leu Val Val Met Glu<br>                  1065                  1070                 1075 | 3312 |
| CTG ATG GCT CAC GGA GAC CTG AAG AGC TAC CTC CGT TCT CTG CGG CCA<br>Leu Met Ala His Gly Asp Leu Lys Ser Tyr Leu Arg Ser Leu Arg Pro<br>          1080                  1085                 1090 | 3360 |
| GAG GCT GAG AAT AAT CCT GGC CGC CCT CCC CCT ACC CTT CAA GAG ATG<br>Glu Ala Glu Asn Asn Pro Gly Arg Pro Pro Pro Thr Leu Gln Glu Met<br>1095                    1100                  1105 | 3408 |

| | | |
|---|---|---|
| ATT CAG ATG GCG GCA GAG ATT GCT GAC GGG ATG GCC TAC CTG AAC GCC<br>Ile Gln Met Ala Ala Glu Ile Ala Asp Gly Met Ala Tyr Leu Asn Ala<br>1110                        1115                    1120                     1125 | | 3456 |
| AAG AAG TTT GTG CAT CGG GAC CTG GCA GCG AGA AAC TGC ATG GTC GCC<br>Lys Lys Phe Val His Arg Asp Leu Ala Ala Arg Asn Cys Met Val Ala<br>                  1130                    1135                    1140 | | 3504 |
| CAT GAT TTT ACT GTC AAA ATT GGA GAC TTT GGA ATG ACC AGA GAC ATC<br>His Asp Phe Thr Val Lys Ile Gly Asp Phe Gly Met Thr Arg Asp Ile<br>                1145                    1150                    1155 | | 3552 |
| TAT GAA ACG GAT TAC TAC CGG AAA GGG GGC AAG GGT CTG CTC CCT GTA<br>Tyr Glu Thr Asp Tyr Tyr Arg Lys Gly Gly Lys Gly Leu Leu Pro Val<br>            1160                    1165                    1170 | | 3600 |
| CGG TGG ATG GCA CCG GAG TCC CTG AAG GAT GGG GTC TTC ACC ACT TCT<br>Arg Trp Met Ala Pro Glu Ser Leu Lys Asp Gly Val Phe Thr Thr Ser<br>          1175                    1180                    1185 | | 3648 |
| TCT GAC ATG TGG TCC TTT GGC GTG GTC CTT TGG GAA ATC ACC AGC TTG<br>Ser Asp Met Trp Ser Phe Gly Val Val Leu Trp Glu Ile Thr Ser Leu<br>1190                      1195                    1200                    1205 | | 3696 |
| GCA GAA CAG CCT TAC CAA GGC CTG TCT AAT GAA CAG GTG TTG AAA TTT<br>Ala Glu Gln Pro Tyr Gln Gly Leu Ser Asn Glu Gln Val Leu Lys Phe<br>                  1210                    1215                    1220 | | 3744 |
| GTC ATG GAT GGA GGG TAT CTG GAT CAA CCC GAC AAC TGT CCA GAG AGA<br>Val Met Asp Gly Gly Tyr Leu Asp Gln Pro Asp Asn Cys Pro Glu Arg<br>              1225                    1230                    1235 | | 3792 |
| GTC ACT GAC CTC ATG CGC ATG TGC TGG CAA TTC AAC CCC AAG ATG AGG<br>Val Thr Asp Leu Met Arg Met Cys Trp Gln Phe Asn Pro Lys Met Arg<br>        1240                    1245                    1250 | | 3840 |
| CCA ACC TTC CTG GAG ATT GTC AAC CTG CTC AAG GAC GAC CTG CAC CCC<br>Pro Thr Phe Leu Glu Ile Val Asn Leu Leu Lys Asp Asp Leu His Pro<br>                1255                    1260                    1265 | | 3888 |
| AGC TTT CCA GAG GTG TCG TTC TTC CAC AGC GAG GAG AAC AAG GCT CCC<br>Ser Phe Pro Glu Val Ser Phe Phe His Ser Glu Glu Asn Lys Ala Pro<br>1270                      1275                    1280                    1285 | | 3936 |
| GAG AGT GAG GAG CTG GAG ATG GAG TTT GAG GAC ATG GAG AAT GTG CCC<br>Glu Ser Glu Glu Leu Glu Met Glu Phe Glu Asp Met Glu Asn Val Pro<br>                  1290                    1295                    1300 | | 3984 |
| CTG GAC CGT TCC TCG CAC TGT CAG AGG GAG GAG GCG GGG GGC CGG GAT<br>Leu Asp Arg Ser Ser His Cys Gln Arg Glu Glu Ala Gly Gly Arg Asp<br>              1305                    1310                    1315 | | 4032 |
| GGA GGG TCC TCG CTG GGT TTC AAG CGG AGC TAC GAG GAA CAC ATC CCT<br>Gly Gly Ser Ser Leu Gly Phe Lys Arg Ser Tyr Glu Glu His Ile Pro<br>            1320                    1325                    1330 | | 4080 |
| TAC ACA CAC ATG AAC GGA GGC AAG AAA AAC GGG CGG ATT CTG ACC TTG<br>Tyr Thr His Met Asn Gly Gly Lys Lys Asn Gly Arg Ile Leu Thr Leu<br>          1335                    1340                    1345 | | 4128 |
| CCT CGG TCC AAT CCT TCC TAA<br>Pro Arg Ser Asn Pro Ser<br>1350                    1355 | | 4149 |

(2) INFORMATION FOR SEQ ID NO:2:

(i) SEQUENCE CHARACTERISTICS:
        (A) LENGTH: 1382 amino acids
        (B) TYPE: amino acid
        (D) TOPOLOGY: linear (ii) MOLECULE TYPE: protein (xi) SEQUENCE DESCRIPTION: SEQ ID NO:2:

Met Gly Thr Gly Gly Arg Arg Gly Ala Ala Ala Ala Pro Leu Leu Val
-27          -25                    -20                        -15

-continued

```
Ala Val Ala Ala Leu Leu Leu Gly Ala Gly His Leu Tyr Pro Gly
    -10              -5                   1              5

Glu Val Cys Pro Gly Met Asp Ile Arg Asn Asn Leu Thr Arg Leu His
             10              15                  20

Glu Leu Glu Asn Cys Ser Val Ile Glu Gly His Leu Gln Ile Leu Leu
             25              30                  35

Met Phe Lys Thr Arg Pro Glu Asp Phe Arg Asp Leu Ser Phe Pro Lys
         40              45                  50

Leu Ile Met Ile Thr Asp Tyr Leu Leu Leu Phe Arg Val Tyr Gly Leu
         55              60                  65

Glu Ser Leu Lys Asp Leu Phe Pro Asn Leu Thr Val Ile Arg Gly Ser
 70              75                  80                      85

Arg Leu Phe Phe Asn Tyr Ala Leu Val Ile Phe Glu Met Val His Leu
                 90              95                      100

Lys Glu Leu Gly Leu Tyr Asn Leu Met Asn Ile Thr Arg Gly Ser Val
             105             110                 115

Arg Ile Glu Lys Asn Asn Glu Leu Cys Tyr Leu Ala Thr Ile Asp Trp
         120             125                 130

Ser Arg Ile Leu Asp Ser Val Glu Asp Asn His Ile Val Leu Asn Lys
 135                 140                 145

Asp Asp Asn Glu Glu Cys Gly Asp Ile Cys Pro Gly Thr Ala Lys Gly
150              155                 160                 165

Lys Thr Asn Cys Pro Ala Thr Val Ile Asn Gly Gln Phe Val Glu Arg
                 170                 175                 180

Cys Trp Thr His Ser His Cys Gln Lys Val Cys Pro Thr Ile Cys Lys
             185                 190                 195

Ser His Gly Cys Thr Ala Glu Gly Leu Cys Cys His Ser Glu Cys Leu
         200                 205                 210

Gly Asn Cys Ser Gln Pro Asp Asp Pro Thr Lys Cys Val Ala Cys Arg
 215                 220                 225

Asn Phe Tyr Leu Asp Gly Arg Cys Val Glu Thr Cys Pro Pro Pro Tyr
230                 235                 240                 245

Tyr His Phe Gln Asp Trp Arg Cys Val Asn Phe Ser Phe Cys Gln Asp
                 250                 255                 260

Leu His His Lys Cys Lys Asn Ser Arg Arg Gln Gly Cys His Gln Tyr
             265                 270                 275

Val Ile His Asn Asn Lys Cys Ile Pro Glu Cys Pro Ser Gly Tyr Thr
         280                 285                 290

Met Asn Ser Ser Asn Leu Leu Cys Thr Pro Cys Leu Gly Pro Cys Pro
 295                 300                 305

Lys Val Cys His Leu Leu Glu Gly Glu Lys Thr Ile Asp Ser Val Thr
310                 315                 320                 325

Ser Ala Gln Glu Leu Arg Gly Cys Thr Val Ile Asn Gly Ser Leu Ile
                 330                 335                 340

Ile Asn Ile Arg Gly Gly Asn Asn Leu Ala Ala Glu Leu Glu Ala Asn
             345                 350                 355

Leu Gly Leu Ile Glu Glu Ile Ser Gly Tyr Leu Lys Ile Arg Arg Ser
         360                 365                 370

Tyr Ala Leu Val Ser Leu Ser Phe Phe Arg Lys Leu Arg Leu Ile Arg
 375                 380                 385

Gly Glu Thr Leu Glu Ile Gly Asn Tyr Ser Phe Tyr Ala Leu Asp Asn
390                 395                 400                 405

Gln Asn Leu Arg Gln Leu Trp Asp Trp Ser Lys His Asn Leu Thr Thr
                 410                 415                 420
```

-continued

```
Thr Gln Gly Lys Leu Phe Phe His Tyr Asn Pro Lys Leu Cys Leu Ser
            425                 430                 435

Glu Ile His Lys Met Glu Val Ser Gly Thr Lys Gly Arg Gln Glu
            440                 445                 450

Arg Asn Asp Ile Ala Leu Lys Thr Asn Gly Asp Lys Ala Ser Cys Glu
            455                 460                 465

Asn Glu Leu Leu Lys Phe Ser Tyr Ile Arg Thr Ser Phe Asp Lys Ile
470                 475                 480                 485

Leu Leu Arg Trp Glu Pro Tyr Trp Pro Pro Asp Phe Arg Asp Leu Leu
                    490                 495                 500

Gly Phe Met Leu Phe Tyr Lys Glu Ala Pro Tyr Gln Asn Val Thr Glu
                505                 510                 515

Phe Asp Gly Gln Asp Ala Cys Gly Ser Asn Ser Trp Thr Val Val Asp
            520                 525                 530

Ile Asp Pro Pro Leu Arg Ser Asn Asp Pro Lys Ser Gln Asn His Pro
            535                 540                 545

Gly Trp Leu Met Arg Gly Leu Lys Pro Trp Thr Gln Tyr Ala Ile Phe
550                 555                 560                 565

Val Lys Thr Leu Val Thr Phe Ser Asp Glu Arg Arg Thr Tyr Gly Ala
                570                 575                 580

Lys Ser Asp Ile Ile Tyr Val Gln Thr Asp Ala Thr Asn Pro Ser Val
                585                 590                 595

Pro Leu Asp Pro Ile Ser Val Ser Asn Ser Ser Ser Gln Ile Ile Leu
            600                 605                 610

Lys Trp Lys Pro Pro Ser Asp Pro Asn Gly Asn Ile Thr His Tyr Leu
            615                 620                 625

Val Phe Trp Glu Arg Gln Ala Glu Asp Ser Glu Leu Phe Glu Leu Asp
630                 635                 640                 645

Tyr Cys Leu Lys Gly Leu Lys Leu Pro Ser Arg Thr Trp Ser Pro Pro
                650                 655                 660

Phe Glu Ser Glu Asp Ser Gln Lys His Asn Gln Ser Glu Tyr Glu Asp
                665                 670                 675

Ser Ala Gly Glu Cys Cys Ser Cys Pro Lys Thr Asp Ser Gln Ile Leu
            680                 685                 690

Lys Glu Leu Glu Glu Ser Ser Phe Arg Lys Thr Phe Glu Asp Tyr Leu
            695                 700                 705

His Asn Val Val Phe Val Pro Arg Lys Thr Ser Ser Gly Thr Gly Ala
710                 715                 720                 725

Glu Asp Pro Arg Pro Ser Arg Lys Arg Arg Ser Leu Gly Asp Val Gly
                730                 735                 740

Asn Val Thr Val Ala Val Pro Thr Val Ala Ala Phe Pro Asn Thr Ser
                745                 750                 755

Ser Thr Ser Val Pro Thr Ser Pro Glu Glu His Arg Pro Phe Glu Lys
            760                 765                 770

Val Val Asn Lys Glu Ser Leu Val Ile Ser Gly Leu Arg His Phe Thr
775                 780                 785

Gly Tyr Arg Ile Glu Leu Gln Ala Cys Asn Gln Asp Thr Pro Glu Glu
790                 795                 800                 805

Arg Cys Ser Val Ala Ala Tyr Val Ser Ala Arg Thr Met Pro Glu Ala
                810                 815                 820

Lys Ala Asp Asp Ile Val Gly Pro Val Thr His Glu Ile Phe Glu Asn
                825                 830                 835
```

```
Asn Val Val His Leu Met Trp Gln Glu Pro Lys Glu Pro Asn Gly Leu
        840                 845                 850

Ile Val Leu Tyr Glu Val Ser Tyr Arg Arg Tyr Gly Asp Glu Glu Leu
        855                 860                 865

His Leu Cys Val Ser Arg Lys His Phe Ala Leu Glu Arg Gly Cys Arg
870                 875                 880                 885

Leu Arg Gly Leu Ser Pro Gly Asn Tyr Ser Val Arg Ile Arg Ala Thr
                890                 895                 900

Ser Leu Ala Gly Asn Gly Ser Trp Thr Glu Pro Thr Tyr Phe Tyr Val
                905                 910                 915

Thr Asp Tyr Leu Asp Val Pro Ser Asn Ile Ala Lys Ile Ile Ile Gly
        920                 925                 930

Pro Leu Ile Phe Val Phe Leu Phe Ser Val Val Ile Gly Ser Ile Tyr
        935                 940                 945

Leu Phe Leu Arg Lys Arg Gln Pro Asp Gly Pro Leu Gly Pro Leu Tyr
950                 955                 960                 965

Ala Ser Ser Asn Pro Glu Tyr Leu Ser Ala Ser Asp Val Phe Pro Cys
                970                 975                 980

Ser Val Tyr Val Pro Asp Glu Trp Glu Val Ser Arg Glu Lys Ile Thr
                985                 990                 995

Leu Leu Arg Glu Leu Gly Gln Gly Ser Phe Gly Met Val Tyr Glu Gly
        1000                1005                1010

Asn Ala Arg Asp Ile Ile Lys Gly Glu Ala Glu Thr Arg Val Ala Val
        1015                1020                1025

Lys Thr Val Asn Glu Ser Ala Ser Leu Arg Glu Arg Ile Glu Phe Leu
1030                1035                1040                1045

Asn Glu Ala Ser Val Met Lys Gly Phe Thr Cys His His Val Val Arg
                1050                1055                1060

Leu Leu Gly Val Val Ser Lys Gly Gln Pro Thr Leu Val Val Met Glu
                1065                1070                1075

Leu Met Ala His Gly Asp Leu Lys Ser Tyr Leu Arg Ser Leu Arg Pro
        1080                1085                1090

Glu Ala Glu Asn Asn Pro Gly Arg Pro Pro Thr Leu Gln Glu Met
        1095                1100                1105

Ile Gln Met Ala Ala Glu Ile Ala Asp Gly Met Ala Tyr Leu Asn Ala
1110                1115                1120                1125

Lys Lys Phe Val His Arg Asp Leu Ala Ala Arg Asn Cys Met Val Ala
                1130                1135                1140

His Asp Phe Thr Val Lys Ile Gly Asp Phe Gly Met Thr Arg Asp Ile
                1145                1150                1155

Tyr Glu Thr Asp Tyr Tyr Arg Lys Gly Gly Lys Gly Leu Leu Pro Val
        1160                1165                1170

Arg Trp Met Ala Pro Glu Ser Leu Lys Asp Gly Val Phe Thr Thr Ser
1175                1180                1185

Ser Asp Met Trp Ser Phe Gly Val Val Leu Trp Glu Ile Thr Ser Leu
1190                1195                1200                1205

Ala Glu Gln Pro Tyr Gln Gly Leu Ser Asn Glu Gln Val Leu Lys Phe
                1210                1215                1220

Val Met Asp Gly Gly Tyr Leu Asp Gln Pro Asp Asn Cys Pro Glu Arg
                1225                1230                1235

Val Thr Asp Leu Met Arg Met Cys Trp Gln Phe Asn Pro Lys Met Arg
        1240                1245                1250

Pro Thr Phe Leu Glu Ile Val Asn Leu Leu Lys Asp Asp Leu His Pro
        1255                1260                1265
```

```
Ser Phe Pro Glu Val Ser Phe Phe His Ser Glu Glu Asn Lys Ala Pro
1270                1275                1280                1285

Glu Ser Glu Glu Leu Glu Met Glu Phe Glu Asp Met Glu Asn Val Pro
                1290                1295                1300

Leu Asp Arg Ser Ser His Cys Gln Arg Glu Glu Ala Gly Gly Arg Asp
            1305                1310                1315

Gly Gly Ser Ser Leu Gly Phe Lys Arg Ser Tyr Glu Glu His Ile Pro
        1320                1325                1330

Tyr Thr His Met Asn Gly Gly Lys Lys Asn Gly Arg Ile Leu Thr Leu
    1335                1340                1345

Pro Arg Ser Asn Pro Ser
1350                1355

(2) INFORMATION FOR SEQ ID NO:3:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:3:

CACTGACCTC ATGCGCATGT GCTGG                                          25

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:4:

ATTGGACCGA GGCAAGGTCA GAAT                                           24

(2) INFORMATION FOR SEQ ID NO:5:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Probe"

(xi) SEQUENCE DESCRIPTION: SEQ ID NO:5:

ATGTGTGTGC AAGGGATGT                                                 19
```